(12) United States Patent
Baltzer

(10) Patent No.: US 8,436,138 B2
(45) Date of Patent: May 7, 2013

(54) BINDER FOR C-REACTIVE PROTEIN

(75) Inventor: Lars Baltzer, Uppsala (SE)

(73) Assignee: Modpro AB, Uppsala (SE)

( * ) Notice: Subject to any disclaimer, the term of this patent is extended or adjusted under 35 U.S.C. 154(b) by 0 days.

(21) Appl. No.: 13/218,875

(22) Filed: Aug. 26, 2011

(65) Prior Publication Data

US 2012/0053124 A1 Mar. 1, 2012

Related U.S. Application Data

(62) Division of application No. 12/225,386, filed as application No. PCT/SE2007/050227 on Apr. 10, 2007, now Pat. No. 8,017,347.

(30) Foreign Application Priority Data

Apr. 7, 2006 (SE) .................................. 0600794-2

(51) Int. Cl.
*A61K 38/00* (2006.01)

(52) U.S. Cl.
USPC ......................................................... 530/324

(58) Field of Classification Search ........................ None
See application file for complete search history.

(56) References Cited

U.S. PATENT DOCUMENTS

| 7,569,661 B2 | 8/2009 | Baltzer et al. |
| 2003/0171251 A1 | 9/2003 | Pepys |
| 2005/0245727 A1 | 11/2005 | Baltzer et al. |

FOREIGN PATENT DOCUMENTS

| EP | 1076240 A1 | 2/2001 |
| WO | WO 03044042 A1 | 5/2003 |
| WO | WO 2004076486 A1 | 9/2004 |

OTHER PUBLICATIONS

Wang et al 2001. J. Biol Chem. 276:49213-49220.*
European Search Report dated Jul. 7, 2010, issued in corresponding European Patent Application 07748388.1-2405.
International Search Report issued in PCT/SE2007/050227 dated Jul. 31, 2007.
Agrawal, A., et al., *Topology and Structure of the C1q-Binding Site on C-Reactive Protein*, The Journal of Immunology, 2001, 166: 3998-4004.
Andersson, M., et al., *Characterization of Surface-Modified Nanoparticles for in Vivo Biointeraction. A Sedimentation Field Flow Fractionation Study*, Anal. Chem. 2005, 77, 5488-5493.
Bartlett, P.A., et al., Total synthesis of (.+−.)-*methyl shikimate and* (.+−.)-*3-phosphoshikimic acid*, J. Am. Chem. Soc., 1984, 106 (25), 7854-7860.
Bohner, M., et al., *Fibrinogen adsorption by PS latex particles coated with various amounts of a PEO/PPO/PEO triblock copolymer*, J. Biomater. Sci. Polymer Edn., 2002, vol. 13, No. 6, pp. 773-746.
Bowie, James U., *Deciphering the Message in Protein Sequences: Tolerance to Amino Acid Substitutions*, 247(4948) Science 1306-1310 (Mar. 16, 1990).
Brown, E.G., et al., *Alkylation of Rink's Amide Linker on Polystyrene Resin: A reductive Amination Approach to Modified Amine-Linkers for the Solid Phase Synthesis of N-Substitute Amide Derivatives*, Tetrahedron Letters, 1997, vol. 38, No. 49, pp. 8457-8460.
Cai, J., et al., *A novel traceless solid phase tertiary amine synthesis based on Merrifield resin*, Tetrahedron Letters 42, 2001, pp. 1383-1385.
Chan, W.C., et al., *Fmoc Solid Phase Peptide Synthesis, A Practical Approach*, 2000, pp. 55-56, Oxford University Press, Oxford, UK.
Orla Deegan et al., *Quantitative detection of C-reactive protein using phosphocholine-labelled enzyme or microspheres*, 312 Analytical Biochemistry 175-181 (2003).
Fowler, P.A., et al., *Synthesis and Biological Activity of Acyclic Analogues of Nojirimycin*, J. Chem. Soc. Perkin Trans. 1, 1994, 2229-2235.
Gabay, Cem, *Acute-Phase Proteins and Other Systemic Responses to Inflammation*, 340(6) The New England Journal of Medicine 448-454 (Feb. 11, 1999).
Hansen, H.J., et al., *Solving the Problem of Antibody Interference in Commercial Sandwich-Type Immunoassays of Carcinoembryonic Antigen*, Clin. Chem. vol. 35, No. 1, (1989), 146-151.
Jain, R.P., et al., *Asymmetric synthesis of (S)-(+)-carnitine and analogs*, Tetrahedron 57 (2001) 6505-6509.
Kamitani, A., et al., *Palladium-Catalyzed Carbonylation of 2-(Propargyl)allyl Phosphates Leading to Highly Unsaturated γ-Lactones*, Angew. Chem. Int. Ed., vol. 42, No. 12, 1397-1399, 2003.
Kim, S., et al., *A simple and mild esterification method for carboxylic acids using mixed carboxylic-carbonic anhydrides*, J. Org. Chem., 1985, 50 (5), 560-565.
McKenna, C.E., et al., *The facile dealkylation of phosphonic acid dialkyl esters by bromotrimethylsilane*, Tetrahedron Letters, No. 2, 1977, pp. 155-158.
Moseley, K.R., et al., *An assay for the detection of human anti-murine immunoglobulins in the presence of CA125 antigen*, J. Immunol. Methods, 106 (1988), 1-6.
Ngo, J. Thomas, *Computational Complexity, Protein Structure Prediction, and the Levinthal Paradox*, Birkhauser Boston 433-506 (1994).
Nygren, P.-A., et al., *Binding proteins from alternative scaffolds*, J. Immunol. Methods, 290 (2004), 3-28.
Rahal, S., et al., *The Eschweiler-Clarke methylation of amino acids*, J. Soc. Alg. Chim.,1994, 4(1), pp. 75-85.
Stults, Nancy L. et al. "*Preparation of Phosphorylcholine Derivatives of Bovine Serum Albumin and Their Application to the Affinity Chromatography of C-Reactive Protein*," 161 Analytical Biochemistry 567-573 (1987).
Tamamura, H., et al., *Disulfide bond-forming reaction using a dimethyl sulfoxide/aqueous HCl system and its application to regioselective two disulfide bond formation*, Int. J. Peptide Protein Res. 45, 1995, pp. 312-319.
Wells, James A., *Additivity of Mutational Effects in Proteins*, 29(37) Biochemistry 8509-8517 (Sep. 18, 1990).

* cited by examiner

*Primary Examiner* — Shulamith H Shafer
(74) *Attorney, Agent, or Firm* — Buchanan Ingersoll & Rooney PC

(57) ABSTRACT

Isolated polypeptides comprising one or more of SEQ ID NOs 3-18, which show a specific binding for C-reactive protein (CRP). A library of isolated polypeptides comprising the polypeptides of SEQ ID NOs 3-18 is disclosed, as are compositions comprising such polypeptides.

7 Claims, 6 Drawing Sheets

Figure 1

BINDER FOR C-REACTIVE PROTEIN

CROSS-REFERENCE TO RELATED APPLICATIONS

This application is a Divisional Application of U.S. patent application Ser. No. 12/225,386, filed on Nov. 12, 2008, now U.S. Pat. No. 8,017,347, issued on Sep. 13, 2011, which is a U.S. National Phase under 35 U.S.C. §371 of International Patent Application No. PCT/SE2007/050277, filed on Apr. 10, 2007, and published on Oct. 18, 2007, as WO 2007/117215 and claims priority to Swedish Patent Application No. 0600794-2, filed on Apr. 7, 2006, all of which are incorporated herein by reference in their entireties for all purposes.

FIELD OF THE INVENTION

The present invention relates to the field of molecules binding specifically to a certain protein, in this case C-reactive protein, and uses thereof.

BACKGROUND OF THE INVENTION

The de novo design of folded polypeptides aims at improving our understanding of protein structure, and also provides a platform for the engineering of new proteins with tailored functions. Designed, folded polypeptides that undergo pH-controlled, site-selective self-functionalization with ligands constitute an excellent toolbox for the construction of various complex molecular systems, e.g. model glycoproteins or complex receptors.

The object of international patent publication WO03/080653 was to provide folded, ligand modified helix-loop-helix polypeptide scaffolds that connect the key biosensing events of recognition and reporting. The well characterized interaction between the enzyme human carbonic anhydrase II, HCAII, and its inhibitor 4-carboxybenzenesulfonamide was selected for a proof of principle demonstration.

C-reactive protein is a plasma protein that circulates in the blood stream in increased amounts during inflammation and after tissue damage. CRP-levels are measured for assessment of i.a. inflammation and increased risk of cardiovascular disease. It is also of interest to measure CRP-levels during heart surgery.

SUMMARY OF THE INVENTION

The present invention relates to polypeptide scaffolds further modified to specifically bind to C-Reactive Protein (CRP). Such modified polypeptide scaffolds are hereinafter referred to as "CRP-specific binders", "CRP-binders" or simply "binders", which terms are used interchangeably unless otherwise indicated.

In a first aspect, the invention relates to CRP-specific binders comprising a polypeptide having a sequence according to SEQ ID NO: 1, wherein at least one phosphocholine derivative is attached to said polypeptide and to a polypeptide scaffold consisting of a four-helix bundle formed of dimers of polypeptides having the sequence according to SEQ ID NO: 1, which binders are modified by incorporation of a binding moiety comprising a phosphocholine derivative and optionally a reporter group that can give a detectable signal. The two protomers of the dimer may be covalently attached to each other through, for example, a disulfide bond, but may also be non-covalently bound to each other. The individual protomers may also be used as binders.

The invention also relates to a method for producing the polypeptide according to the first embodiment, said method comprising the steps
- synthesizing a polypeptide having the sequence according to SEQ ID NO: 1;
- bringing a phosphocholine derivative in contact with an unblocked lysine of said polypeptide under conditions suitable for the attachment of the phosphocholine derivative to the lysine;
- optionally bringing a reporter group in contact with an unblocked lysine of said polypeptide under conditions suitable for the attachment of the reporter group to the lysine.

In a further aspect the invention relates to the use of binders according to the first aspect in therapeutic and diagnostic applications, such as the incorporation of such binders in pharmaceutical or diagnostic compositions, assays for determining the concentration of CRP in a sample, e.g. from a patient undergoing heart surgery or suspected of having an inflammation, and in biotechnological applications, such as protein purification or binding assays.

BRIEF DESCRIPTION OF THE FIGURES

FIG. 1 is an overview of a library of peptide scaffolds used in the present invention.

DETAILED DESCRIPTION OF THE INVENTION

Figure 2:
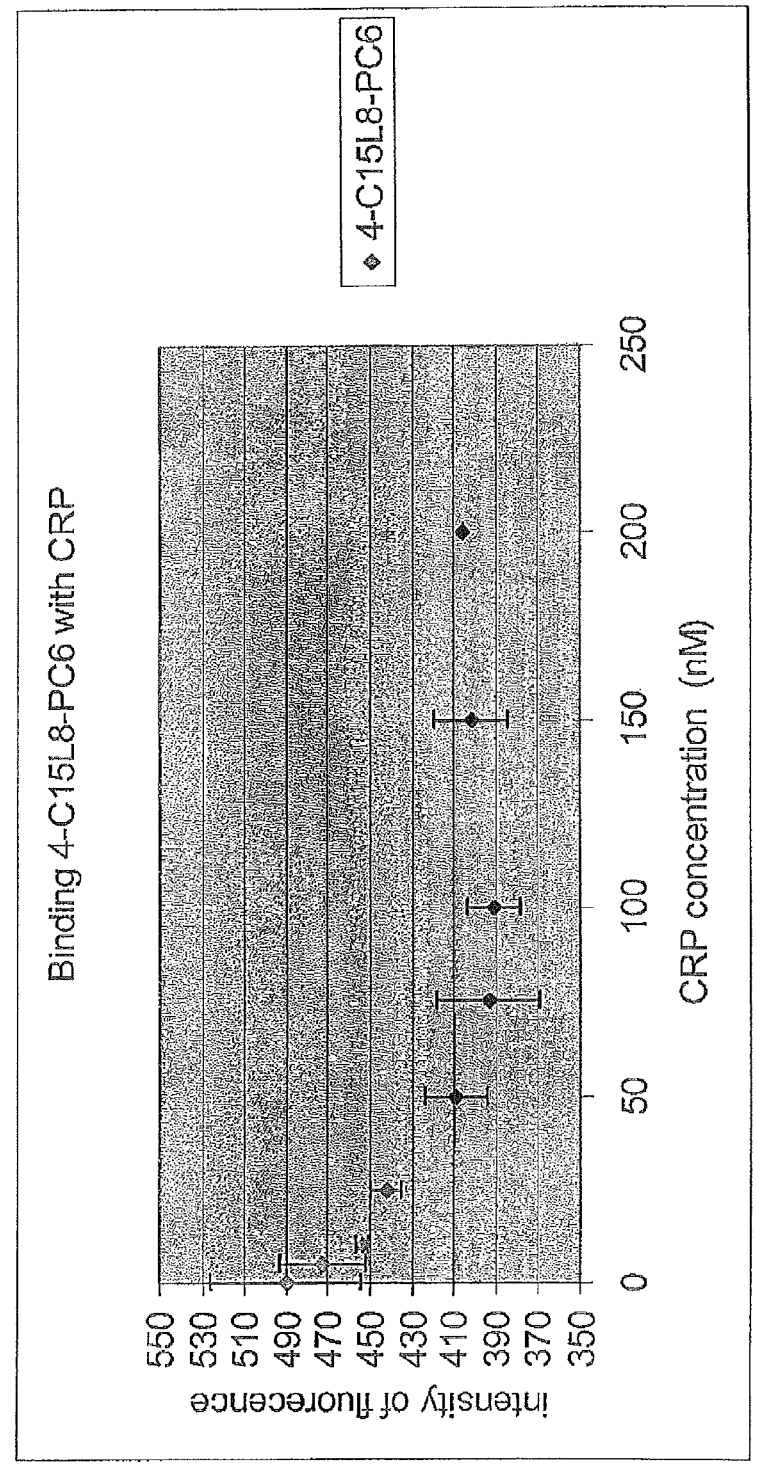
FIG. 2 shows the affinity of a CRP-binder of the present invention to CRP.

It has been surprisingly shown by the present inventors that the binding affinity between CRP and a polypeptide scaffold may be dramatically enhanced by attaching a phosphocholine derivative in certain positions. Phosphocholine alone has a binding affinity of ~1 µM and the scaffold polypeptides have a binding affinity of ~100-1000 µM, while the polypeptides modified with a phosphocholine derivative have a binding affinity for CRP in the nanomolar range.

The unmodified scaffold binds to the surface of CRP and the phosphocholine derivative should be introduced in a position within, or in close proximity of, the binding site on the polypeptide scaffold. In order to reach its binding site on CRP, the phosphocholine derivative may comprise a spacer of 1-12 carbon atoms, i.e. 1, 2, 3, 4, 5, 6, 7, 8, 9, 10, 11 or 12 carbon atoms.

A further surprising advantage of the binders of the present invention is that they bind with high affinity to CRP from different mammals, in contrast to CRP-specific antibodies that usually bind with high affinity to CRP from one mammalian species but with lower affinity to CRP from other species.

The polypeptide scaffold may also be varied with regard to charge in order to optimize binding affinity to CRP. This is preferably done by exchanging a charged amino acid residue for an uncharged residue, or a residue with different charge, in the polypeptide, or vice versa. For example, a Val or Ala (uncharged) can be exchanged for a Glu (charge −1) or an Arg (charge +1).

According to one embodiment of the present invention, the polypeptide scaffold has at least two lysine residues to which a CRP-binding moiety and a reporter group, respectively, may be attached.

The basic polypeptide scaffold protomer has the sequence according to SEQ ID NO: 1. This protomer can be produced by any method known to the person skilled in the art, such as by recombinant technology or conventional automated solid phase peptide synthesis. One or more positions should carry a lysine. These positions are preferably selected from positions 8, 10, 15, 17, 22, 25, 34 and 37. The CRP-binding moiety and the optional reporter group are then attached to the lysines according to the method discussed below.

The reporter group may be any group that can be attached to a lysine residue and give a detectable signal. Preferred examples of reporter groups are fluorescent probes such as dansyl, coumarin, fluorescein, rhodamine and Oregon Green derivatives. The reporter group may also be an enzyme such as phosphoenolpyruvate kinase or a detectable particle such as a gold nanoparticle. The reporter group is attached to the lysine residue according to the supplier's instructions or by other conventional methods. Preferably, the reporter group is attached to the protomer while the newly synthesized protomer is still on the resin.

The CRP-binding moiety is a phosphocholine derivative comprising a phosphocholine moiety and a spacer. The length of the spacer depends on where the ligand is attached to the scaffold and where the ligand binds to CRP. The spacer is usually an aliphatic chain of 1-12 carbon atoms optionally substituted with hydrophilic groups to enhance solubility.

The phosphocholine derivative is attached to the protomer by bringing the protomer into contact with an active ester of the phosphocholine derivative. The active ester has the general formula

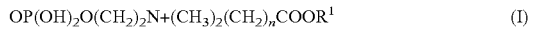

$$OP(OH)_2O(CH_2)_2N+(CH_3)_2(CH_2)_nCOOR^1 \quad (I)$$

wherein $1 \leq n \leq 12$ and $R^1$ is a leaving group with a $pK_a$ of about 6-8. The synthesis of active esters wherein n is 4, 6 or 11 and $R^1$ is p-nitro-phenyl are described in the experimental section below.

The phosphocholine derivative is incorporated into the polypeptide scaffold as disclosed in the experimental section.

The CRP-binder of the present invention may also be bound to a solid support, optionally through a linker. A number of solid supports, such as chips, plates, beads and membranes, and linkers are commercially available and may be combined by the skilled person depending on the circumstances the CRP-binder of the invention is to be used under.

Binding Assays

One aspect of this invention relates to binding assays using the binders of the present invention, and, more particularly, to a method for eliminating interference resulting from rheumatoid factors or human anti-mouse antibodies (HAMA) in biological samples.

Different types of sandwich assays are widely used. One of the most common is sandwich ELISA where an antibody is used to capture the antigen and another labelled antibody is used to detect the bound antigen. Both of these antibodies are usually of mammalian origin. In such assays anti-mammalian IgG antibodies present in the samples, which often are derived from body fluids such as blood or serum, may simulate the behaviour of the antigen by linking the detection antibody to the capture antibody, thus causing false positive reactions. Such false positive reactions are observed in sandwich assays based on both polyclonal and monoclonal antibodies.

An increasing number of patients are given mouse monoclonal antibodies for diagnosis or therapy. Monoclonal antibody administration often induces an antibody response in the patients[12]; human anti-murine antibodies (HAMA) are produced. Sandwich-type assays based on mouse monoclonal antibodies are known to give false positive results when HAMA is present in the serum of the patient. This will be an increasing problem in the clinical chemistry laboratory as the number of patients treated with monoclonal antibodies increases.

Rheumatoid factor (RF) is also a major source of interference in many immunoassays. RF is an autoantibody that reacts with the Fc portion of mammalian IgG. RF can be of the IgA, IgG, or IgM classes. Between 60% and 80% of patients with Rheumatoid Arthritis (RA) have RF activity in their serum. RF has also been found in serum from patients with other connective tissue diseases and in many other diseases. Although RF reacts with the Fc-part of IgG, they display heterogeneity in their reactivity to IgG of different species. This reactivity to IgG of other species may produce false reactions in assays involving antibodies. The classical tests for RF are agglutination tests, in which the RF reacts with two (or more if it is an IgM-RF) different mammalian IgG molecules, thus causing agglutination. The same reaction will give a false-positive reaction in a sandwich ELISA, owing to the binding of detection antibody to capture antibody in the absence of the antigen that the assay was designed to detect.

One approach to the above problem is the use of Fab fragments in the assay, because the anti-IgG antibodies are usually directed against the Fc part of the IgG molecule. However, the digestion of IgG to produce pure Fab fragments is time consuming and usually results in loss of antibody titre and will not reduce the interference caused by anti-Fab antibodies. Furthermore, addition of mouse IgG or mouse serum or chromatography to remove the interfering antibodies have been used to avoid the above mentioned problem. Addition of normal mouse IgG or normal mouse serum sometimes fails to eliminate the false positive reaction. Removal of interfering antibodies by chromatography is time consuming and less suitable for routine analysis.

One aspect of the present invention is therefore to change at least one of the antibodies in the assay to a binder according to the invention that is not bound to by HAMA or RF.

In one embodiment of this aspect, the invention relates to a method for assaying the concentration of C-reactive protein in a sample, comprising the steps
  bringing the sample in contact with a first polypeptide dimer according to any of claims 1-6, said first polypeptide being bound to a solid support;
  bringing the sample in contact with a second polypeptide diner according to any of claims 3-6 having a reporter group attached to it; and
  detecting the presence or absence of the reporter group on said second polypeptide dimer.

EXPERIMENTAL SECTION

Synthesis of Phosphocholine Derivatives PC6, PC11 and PC4

The phosphocholine derivative to be attached to the polypeptide scaffold may have a spacer of 1-12 carbon atoms, as explained above. These are denoted PC, for phosphocholine, followed by a number giving the length of the spacer, i.e PC6 has a spacer of 6 carbon atoms.

For the synthesis of PC6 we originally chose a simple and short route as outlined in Scheme 1. In the first step 6-dimethylamino hexanoic acid was prepared by alkylation of the corresponding amino acid with formaldehyde under catalytic hydrogenation conditions in good yield. The resulting tertiary amine was simply purified with a strong acidic cation exchanger.[3] The carboxylic acid function was then esterified to form the methyl ester in essentially quantitative yield and no purification step was required. The subsequent alkylation with the bromide, which was easily prepared from diethyl chlorophosphate and 2-bromo ethanol,[4] proceeded usually with only moderate yields. After RP HPLC purification the methyl ester Was cleaved with Lithium hydroxide and the carboxylic acid was obtained in almost quantitative yield and purification was not necessary. The generation of the active ester was done following a procedure of Kim et al. utilizing p-nitrophenyl chlorofomate, a base and DMAP.[5] The active ester was obtained after RP HPLC purification in 28% yield only. The final deprotection of the phosphate group was done under mild conditions with TMSBr without affecting the carboxylic ester.[6] On the other hand, the formation of side products for some substrates during this reaction is a known disadvantage of this procedure.[7] However, we obtained the desired phosphate in 25% yield besides the mono-deprotected phosphate and the quaternary amine without phosphate group.

For the preparation of PC11 we chose a synthetic route including some steps on solid phase in order to avoid cumbersome purification procedures and solubility problems (Scheme 2). Fmoc-protected imdecanoic acid was therefore coupled to Wang resin utilizing the DIC method in 66% yield.[8] After deprotection with piperidine the dimethylation was accomplished with formic acid and sodium borohydride.[9] The alkylation step to the quaternary amine was a sluggish reaction and needed 10 equivalents of the bromide and heating for 4 days.[10] After cleavage from the resin the crude product was transformed to the active ester by the same method that we used for PC6. The final deprotection step of the phosphate group proceeded similarly to PC6 with formation of byproducts, but 27% of the desired product were obtained.

Scheme 1
PC6-pNitrophenylester Synthesis

Phosphoric acid 2-bromo-ethyl ester diethyl ester. A solution of 2-bromo ethanol (1.42 mL, 20 mmol) and dry pyridine (3.23 mL, 40 mmol) in dry dichloromethane (25 mL) was cooled to 0° C. Diethyl chlorophosphate (3.36 mL, 23 mmol) was added dropwise and the reaction mixture was stirred at room temperature for 24 h. Diethyl ether (40 mL) and 1 N HCl (40 mL) were added and the organic layer was separated and washed consecutively with 1 N HCl and saturated NaHCO3 and dried over MgSO4. After evaporation of the solvents the residue was purified by column chromatography (silica gel, ethyl acetate/pentane 1:1) to give the product (4.85 g, 18.6 mmol, 93%) as light yellowish oil. $^1$H NMR (CDCl$_3$, 400 MHz) δ=1.34 (dt, 6H, 2×CH$_3$, $^3$J(H,H)=7.2 Hz, $^4$J(H,P)=1.2 Hz); 3.52 (t, 2H, CH$_2$Br, $^3$J=6 Hz); 4.13 (dq, 4H, 2×CH$_2$CH$_3$, $^3$J(H,H)=7.2 Hz, $^3$J(H,P)=7.2 Hz); 4.28 (dt, 4H, 2×OCH$_2$CH$_2$Br, $^3$J(H,H)=6.4 Hz, $^3$J(H,P)=8.4 Hz). $^{13}$C NMR (CDCl$_3$, 100.5 MHz) δ=16.0 (d, 2×CH$_3$, $^3$J=6.8 Hz); 29.4 (d, CH$_2$Br, $^2$J=7.6 Hz); 64.0 (d, OCH$_2$, $^2$J=5.3 Hz); 66.5 (d, OCH$_2$, $^2$J=5.3 Hz).

6-dimethylamino hexanoic acid. A solution of the amino acid (1.32 g, 10 mmol) in water was hydrogenated in a Parr apparatus in the presence of an excess of formaldehyde (4 mL) and 10% Pd/C (0.5 g) at 90 psi of H2 at room temperature for 36 h. The catalyst was removed by filtration and was washed twice with hot water. The combined aqueous layer was passed through a DOWEX 50WX2-100 ion exchanger column. After washing with water the column was eluted with 2% of aqueous NH4OH to give the pure product (1.39 g, 8.7 mmol, 87%) as colorless crystals.

6-dimethylamino hexanoic acid methyl ester. To an ice-cold solution of 6-dimethylamino hexanoic acid (1.37 g, 8.6 mmol) in dry methanol (50 mL) was added thionylchloride (9 mL) dropwise over 30 min. The reaction mixture was warmed to room temperature and was stirred over night. The solvent was evaporated under reduced pressure. Repeated addition of methanol and subsequent evaporation gave the methyl ester in almost quantitative yield in pure form as colorless solid. $^1$H NMR (DMSO d$_6$, 400 MHz) δ=1.27 (m, 2H, CH$_2$); 1.53 (m, 2H, CH$_2$); 1.63 (m, 2H, CH$_2$); 2.31 (t, 2H, $^3$J=7.6 Hz, CH$_2$); 2.67 (s, 6H, N(CH$_3$)$_2$); 2.96 (t, 2H, $^3$J=8 Hz, CH$_2$); 3.57 (s, 3H, COOCH$_3$). $^{13}$C NMR (DMSO d$_6$, 100.5 MHz) δ=23.1; 23.8; 25.3; 32.9; 41.7; 51.2; 56.0; 173.1.

[2-Diethoxy-phosphoryloxy)-ethyl]-(5-methoxycarbonyl-pentyl)-dimethylammonium trifluoroacetate. The methyl ester (1.73 g, 10 mmol) was dissolved in dry acetonitrile (15 mL) and K$_2$CO$_3$ (1.38 g, 10 mmol) was added. This suspension was refluxed under nitrogen gas for 36 h. After cooling to room temperature water was added and the pH was adjusted to 2 by adding TFA. The solution was purified by rp HPLC (Supelco Discovery C18, 21.2 mm×15 cm, 5 µm, A: 5% IPA, 95% H$_2$O, 0.1% TFA, B: 90% IPA, 10% H$_2$O, 0.1% TFA, 0 to 15% B over 14 min, $t_R$=11.8 min) and lyophilized to give the TFA salt of the quaternary amine as light yellow oil (1.06 g, 3.0 mmol, 30%). LC-MS (Phenomenex Gemini, C18, 5 µm, 150×3.0 mm, A: 0.1% formic acid in water, B: 0.1% formic acid in acetonitrile, 10-50% B over 10 min) $t_R$=6.4 min (LSD signal), m/z=354.2 for [M±H]$^+$. $^1$NMR (CD$_3$OD, 400 MHz) δ=1.41-1.50 (m, 8H, 2×OCH$_2$CH$_3$ and CH$_2$); 1.77 (m, 2H, CH$_2$); 1.90 (m, 2H, CH$_2$); 2.44 (t, 2H, CH$_2$, $^3$J=7.2 Hz); 3.25 (s, 6H, N(CH$_3$)$_2$); 3.48 (m, 2H, CH$_2$); 3.72 (s, 3H, COOCH$_3$) 3.82 (m, 2H, CH$_2$); 4.26 (dq, 4H, 2×CH$_2$CH$_3$, $^3$J(H,H)=6.8 Hz, $^3$J(H,P)=8.0 Hz); 4.58 (brs, 2H, CH$_2$). $^{13}$C NMR (CD$_3$OD, 100.5 MHz) δ=16.4 (d, 2×OCH$_2$CH$_3$, $^3$J=6.1 Hz); 23.3 (CH$_2$); 25.3 (CH$_2$); 26.7 (CH$_2$); 34.4 (CH$_2$); 52.0 (CH$_3$); 52.2 (CH$_3$); 62.1 (d, CH$_2$, $^2$J=5.3 Hz); 64.8 (CH$_2$); 66.1 (d, CH$_2$, $^2$J=6.1 Hz); 66.7 (CH$_2$); 175.5 (CO).

(5-carboxy-pentyl)-[2-(diethoxy-phosphoryloxy)-ethyl]-dimethylammonium trifluoroacetate. The TFA salt of the quaternary amine (200 mg, 0.56 mmol) was dissolved in a mixture of t-butanol/water (2:1, 9 mL) and LiOH.H$_2$O (47 mg, 1.12 mmol) was added. The reaction mixture was stirred for 3 h at room temperature and the organic solvent was removed under reduced pressure. The pH of the aqueous solution was adjusted to 7 with 0.1 N1101 and the mixture was subsequently lyophilized and further used without purification. LC-MS (Phenomenex Gemini, C18, 5 µm, 150×3.0 mm, A: 0.1% formic acid in water, B: 0.1% formic acid in acetonitrile, 10-40% B over 10 min) $t_R$=6.8 min (LSD signal), m/z=340.2 for [M+H]$^+$. $^1$H NMR (CD$_3$OD, 400 MHz) δ=1.34-1.42 (m, 8H, 2×OCH$_2$CH$_3$ and CH$_2$); 1.67 (m, 2H, CH$_2$); 1.80 (m, 2H, CH$_2$); 2.20 (t, 2H, CH$_2$, $^3$J=7.6 Hz); 3.16 (s, 6H, N(CH$_3$)$_2$); 3.40 (m, 2H, CH$_2$); 3.72 (brs, 2H, CH$_2$); 4.18 (dq, 4H, 2×CH$_2$CH$_3$, $^3$J(H,H)=7.0 Hz, $^3$J(H,P)=8.0 Hz); 4.50 (brs, 2H, CH$_2$). $^{13}$C NMR (CD$_3$OD, 100.5 MHz) δ=16.4 (d, 2×OCH$_2$CH$_3$, $^3$J=6.8 Hz); 23.2 (CH$_2$); 26.5 (CH$_2$); 27.1 (CH$_2$); 37.9 (CH$_2$); 52.0 (CH$_3$); 62.1 (d, CH$_2$, $^2$J=4.6 Hz); 64.5 (CH$_2$); 66.1 (d, CH$_2$, $^2$J=6.1 Hz); 66.8 (CH$_2$); 181.3 (CO).

[2-(diethoxy-phosphoryloxy)-ethyl]-dimethyl-[5-(4-nitro-phenoxycarbonyl)-pentyl]-ammonium trifluoroacetate. To a solution of the carboxylic acid (26 mg, 0.076 mmol) in dry acetonitrile (3 mL) were consecutively added triethylamine (0.01 mL, 0.084 mmol), p-nitrophenyl chloroformate (31 mg, 0.15 mmol) and DMAP (1 mg). The reaction was stopped after 4 h by addition of 0.1% TFA in water and subsequently purified by rp HPLC (Supelco Discovery C18, 21.2 mm×15 cm, 5 μm, A: 5% IPA, 95% $H_2O$, 0.1% TFA, B: 90% IPA, 10% $H_2O$, 0.1% TFA, 20 to 40% B over 12 min, $t_R$=10.3 min) to give the p-nitrophenyl ester as colorless oil (10 mg, 0.022 mmol, 28%). LC-MS (Phenomenex C18, 5 μm, 150×3.0 mm, A: 0.1% formic acid in water, B: 0.1% formic acid in acetonitrile, 10-90% B over 8 min) $t_R$=4.3 min (UV signal), m/z=461.5 for $[M+H]^+$. $^1H$ NMR ($CDCl_3$, 300 MHz) δ=1.34 (t, 6H, 2×$OCH_2CH_3$, $^3J$=7.2 Hz); 1.48 (m, 2H, $CH_2$); 1.81 (m, 4H, 2×$CH_2$); 2.63 (t, 2H, $CH_2$, $^3J$=7.2 Hz); 3.27 (s, 6H, $N(CH_3)_2$); 3.51 (m, 2H, $CH_2$); 3.92 (m, 2H, $CH_2$); 4.14 (dq, 4H, 2×$CH_2CH_3$, $^3J(H,H)$=7.5 Hz, $^3J(H,P)$=7.5 Hz); 4.47 (m, 2H, $CH_2$); 7.27 (d, 2H, $^3J$=9 Hz, Phe-H); 8.25 (d, 2H, $^3J$=9 Hz, Phe-H). $^{13}C$ NMR ($CDCl_3$, 75.4 MHz) δ=16.0 (d, 2×$OCH_2CH_3$, $^3J$=6.6 Hz); 22.4 ($CH_2$); 23.8 ($CH_2$); 25.4 ($CH_2$); 33.6 ($CH_2$); 51.6; 60.8 (d, $CH_2$, $^2J$=4.8 Hz); 63.3 (?); 64.7 (d, $CH_2$, $^2J$=5.9 Hz); 65.7; 122.5 (2×Phe-CH); 125.2 (2×Phe-CH); 145.3 (Phe-C); 155.3 (Phe-C); 170.8 (CO).

Dimethyl-[5-(4-nitro-phenoxycarbonyl)-pentyl]-(2-phosphonooxy-ethyl)-ammonium trifluoro acetate. The protected p-nitrophenyl ester (20 mg, 0.043 mmol) was dissolved in dry acetonitrile (3 mL) and trimethyl silylbromide (0.11 mL, 0.87 mmol) was added. The reaction mixture was stirred at room temperature for 24 h. After adding 0.1% TFA in water (1 mL) the solution was purified by rp HPLC (Supelco Discovery C18, 21.2 mm×15 cm, 5 μm, A: 0.1% TFA in water, B: 0.1% TFA in acetonitrile, 17 to 30% B over 14 min, $t_R$=12.7 min) to give the phosphocholine derivative $PC_6$-pNitrophenylester (4.6 mg, 0.011 mmol, 25%) as TFA salt. LC-MS (Phenomenex Gemini, C18, 5 μm, 150×3.0 mm, A: 0.1% formic acid in water, B: 0.1% formic acid in acetonitrile, 10-90% B over 10 min) $t_R$=3.8 min (UV signal), m/z=405.5 for $[M+H]^+$.

Scheme 2

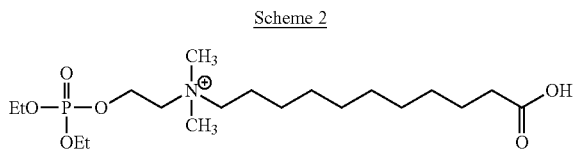 [SMILES: CCOP(=O)(OCC)OCC[N+](C)(C)CCCCCCCCCCC(=O)O]

(10-Carboxy-decyl)-[2-(diethoxy-phosphoryloxy)-ethyl]-dimethyl-ammonium trifluoro acetate Fmoc-undecanoic acid (635 mg, 1.5 mmol) was dissolved in dry DMF (2 ml) and a solution of diisopropyl carbodiimid (0.12 ml, 0.75 mmol) in dry dichloromethane (10 ml) was added. The resulting yellow mixture was stirred at 0° C. for 20 min. After removal of the volatile dichloromethane the solution of the symmetrical anhydride was added to the Wang resin (250 mg, 1.2 mmol/g, 0.3 mmol). DMAP (18 mg, 0.15 mmol) was added and the reaction mixture was stirred over night (W. C. Chan, P. D. White in *Fmoc Solid Phase Peptide Synthesis, A Practical Approach* (Eds.: W. C. Chan, P. D. White) Oxford University Press, Oxford 2000, pp. 55-56.) The resin was washed with DMF (5×2 min), dichloromethane (5×2 min) and was shrunk with diethyl ether. The procedure was repeated one time and the final substitution level of 0.8 mmol/g (66%) was determined based on UV spectrophotometry of the Fmoc-piperidine adduct. (ibid., pp 62-63)

After Fmoc deprotection with 20% piperidine/DMF the resin was swelled in THF. A mixture of THF (2 ml), formaldehyde (40%, 0.7 ml, 1 mmol) and acetic acid (0.7 ml) were added and the resin was incubated for 5 min. Then sodium cyanoborohydrid (62 mg, 1 mmol) was added and the resin was stirred at room temperature over night. Afterwards the resin was washed successively with THF, $H_2O$ and MeOH.

E. G. Brown, J. M. Nuss *Tetrahedron Lett.* 1997, 38, 8457-8460.

The resin was swelled in DMF and phosphoric acid diethyl ester-(2-bromo-ethyl ester)/phosphoric acid 2-bromo-ethyl ester diethyl ester (520 mg, 2 mmol) and DIEA (0.03 ml, 0.2 mmol) were added and the reaction mixture was heated to 60° C. for 4 d. The resin was washed with DMF, DCM and was shrunk with MeOH.

J. Cai, B. Wathey *Tetrahedron Lett.* 2001, 42, 1383-1385.

The product was finally cleaved from the resin by stirring it with a mixture of TFA/$H_2O$/TIS (95:2.5:2.5) for 2 h. The carboxylic acid was used after evaporation of the organic solvents, addition of water and lyophilization without further purification.

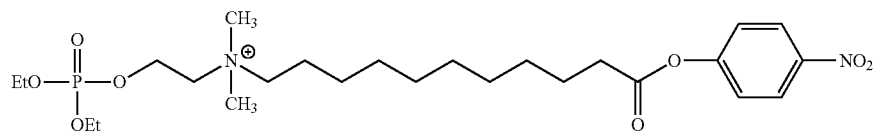 [SMILES: CCOP(=O)(OCC)OCC[N+](C)(C)CCCCCCCCCCC(=O)Oc1ccc([N+](=O)[O-])cc1]

[2-(Diethoxy-phosphoryloxy)-ethyl]-dimethyl-[10-(4-nitro-phenoxycarbonyl)-decyl]-ammonium trifluoro acetate To a solution of the carboxylic acid X in dry acetonitrile (5 ml) were consecutively added triethylamine (0.03 ml, 0.2 mmol), p-nitrophenyl chloroformate (80 mg, 0.39 mmol) and DMAP (7 mg). The reaction was stopped after 4 h by addition of 0.1% TFA in water and subsequently purified by RP HPLC (Supelco Discovery C18, 21.2 mm×15 cm, 5 μm, A: 0.1% TFA in IPA/$H_2O$ 5:95, B: 0.1% TFA in IPA/$H_2O$ 90:10, 15 to 45% B over 20 min, $t_R$=16.5 min) to give the p-nitrophenyl ester X as colorless oil (4 mg, 0.007 mmol, %). LC-MS (Phenomenex Gemini, C18, 5 μm, 150×3.0 mm, A: 0.1% formic acid in water, B: 0.1% formic acid in acetonitrile, 10-90% B over 10 min) $t_R$=5.2 min (UV signal); M=531.5 ($M^+$).

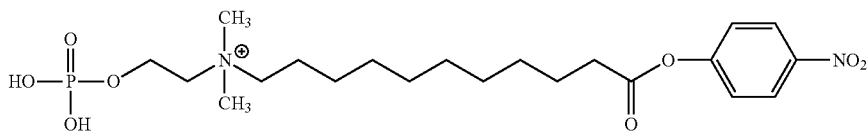 [SMILES: C[N+](C)(CCCCCCCCCCC(=O)Oc1ccc([N+](=O)[O-])cc1)CCOP(=O)(O)O]

Dimethyl-[10-(4-nitro-phenoxycarbonyl)-decyl]-(2-phosphonooxy-ethyl)-ammonium trifluoro acetate The protected p-nitrophenyl ester (4 mg, 0.007 mmol) was dissolved in dry acetonitrile (3 ml) and trimethyl silylbromide (0.11 ml, 0.07 mmol) was added after 0, 12 and 24 hours resp. The reaction mixture was stirred at room temperature for totally 36 h. After adding 0.1% TFA in water (1 ml) the solution was purified by rp HPLC (Hichrom C8, 21.2 mm×25 cm, 10 μm, A: 0.1% TFA in ACN/H$_2$O 10:90, B: 0.1% TFA in ACN/H$_2$O 90:10, 40 to 60% B over 15 min, $t_R$=14.2 min) to give the phosphocholine derivative (1.1 mg, 0.002 mmol, 27%) as TFA salt.

LC-MS (Phenomenex Gemini, C18, 5 μm, 150×3.0 mm, A: 0.1% formic acid in water, B: 0.1% formic acid in acetonitrile, 10-90% B over 10 min) $t_R$=5.9 min (UV signal), M=475.4 (M$^+$).

PC4

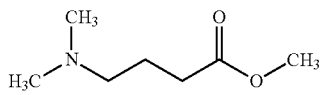

4-dimethylamino butyric acid methyl ester same procedure as for PC6

$^1$H NMR (D$_2$O, 400 MHz) δ=2.06 (m, 2H, CH$_2$); 2.56 (t, 2H, $^3$J=7.2 Hz, CH$_2$); 2.93 (s, 6H, N(CH$_3$)$_2$); 3.22 (m, 2H, CH$_2$); 3.75 (s, 3H, COOCH$_3$).

$^{13}$C NMR (CD$_3$OD, 100.5 MHz) δ=20.9; 31.2; 43.5; 52.3; 58.1; 174.3

LC-MS (Phenomenex Gemini, C18, 5 μm, 150×3.0 mm, A: 0.1% formic acid in water, B: 0.1% formic acid in acetonitrile, 10-50% B over 10 min) $t_R$=1.3 min (ELSD signal); M=146.4 ((M+H)$^+$).

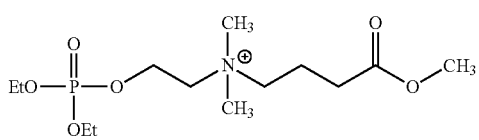 [SMILES: CCOP(=O)(OCC)OCC[N+](C)(C)CCCC(=O)OC]

[2-Diethoxy-phosphoryloxy)-ethyl]-(3-methoxycarbonyl-propyl)-dimethylammonium trifluoroacetate The methyl ester X (516 mg, 3.5 mmol) was dissolved in dry acetonitrile (8 ml) and K$_2$CO$_3$ (484 mg, 3.5 mmol) was added. This suspension was refluxed under nitrogen gas for 24 h. After cooling to room temperature water was added and the pH was adjusted to 2 by adding TFA. The solution was purified by rp HPLC (Supelco Discovery C18, 21.2 mm×15 cm, 5 μm, A: 0.1% TFA, 5% IPA in H$_2$O, B: 0.1% TFA, 10% H$_2$O in IPA, 0 to 10% B over 10 min, $t_R$=8.8 min) and lyophilized to give the TFA salt of the quaternary amine as light yellow oil. $^1$H NMR (CD$_3$OD, 400 MHz) δ=1.36 (t, 6H, 2×OCH$_2$CH$_3$, $^3$J=6.8 Hz); 2.08 (m, 2H, CH$_2$); 2.47 (t, 2H, CH$_2$, $^3$J=7.2 Hz); 3.20 (s, 6H, N(CH$_3$)$_2$); 3.45 (m, 2H, CH$_2$); 3.70 (s, 3H, COOCH$_3$); 3.76 (t, 2H, CH$_2$, $^3$J=4.4 Hz); 4.18 (dq, 4H, OCH$_2$CH$_3$ $^3$J(H,H)=7.2 Hz, $^3$J(H,H)=7.2 Hz); 4.52 (bs, 2H, CH$_2$).

$^{13}$C NMR (CD$_3$OD, 100.5 MHz) δ=16.4 (d, 2×OCH$_2$CH$_3$, $^3$J=6.1 Hz); 19.0 (CH$_2$); 30.7 (CH$_2$); 52.3 (CH$_3$); 52.4 (CH$_3$); 62.1 (d, CH$_2$, $^2$J=4.5 Hz); 64.4 (CH$_2$); 65.4 (CH$_2$); 66.1 (d, CH$_2$, $^2$J=6.0 Hz); 174.0 (CO).

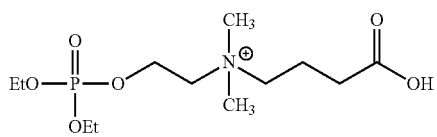 [SMILES: CCOP(=O)(OCC)OCC[N+](C)(C)CCCC(=O)O]

(3-carboxy-propyl)-[2-(diethoxy-phosphoryloxy)-ethyl]-dimethylammonium trifluoroacetate same procedure as for PC6

LC-MS (Phenomenex Gemini, C18, 5 μm, 150×3.0 mm, A: 0.1% formic acid in water, B: 0.1% formic acid in acetonitrile, 10-50% B over 10 min) $t_R$=1.8 min (ELSD signal); M=312.3 (M$^+$).

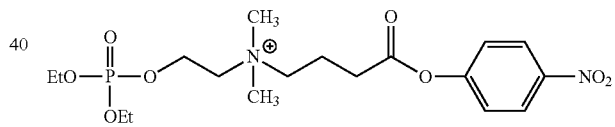

[2-(Diethoxy-phosphoryloxy)-ethyl]-dimethyl-[3-(4-nitro-phenoxycarbonyl)-propyl]-ammonium trifluoroacetate To a solution of the carboxylic acid in dry acetonitrile (5 ml) were consecutively added triethylamine, p-nitrophenyl chloroformate and DMAP. The reaction was stopped after 4 h by addition of 0.1% TFA in water and subsequently purified by RP HPLC (Supelco Discovery C18, 21.2 mm×15 cm, 5 μm, A: 0.1% TFA, 5% IPA in H$_2$O, B: 0.1% TFA 10% H$_2$O in IPA, 10 to 30% B over 13 min, $t_R$=11.8 min) to give the p-nitrophenyl ester as colorless oil.

LC-MS (Phenomenex Gemini, C18, 5 μm, 150×3.0 mm, A: 0.1% formic acid in water, B: 0.1% formic acid in acetonitrile, 10-90% B over 10 min) $t_R$=3.1 Min (UV signal); M=433.2 (M$^+$).

Alternative Scheme for Preparation of PC6

During the priority year, an alternative strategy for preparing the phosphocholine ligand PC6 was developed. This is outlined below. This strategy for preparation of PC6 (compound 9) is outlined in scheme 3. Phosphorylation was chosen as the last step, since this function was considered troublesome, even in a protected form, to carry through other necessary transformation steps.

Commercially available aminohexanoic acid 2 was N,N-dimethylated[11][12] by an Eschweiler-Clarke-type procedure (treatment with formaldehyde and hydrogen/palladium/carbon), and the resulting product (3, 86%) was esterified by treatment with methanolic hydrogen chloride to give the methyl ester 4 (96%). Quartenarization was effected by reacting 4 with monomethoxytrityl-protected bromoethanol 1, forming derivative 5 (73%). Unprotected bromoethanol could also be reacted with 4, but the reaction yield was lower and the product was more difficult to detect and purify. Monomethoxytrityl protection conferred lipophilicity and TLC detectability (UV visible and acid stainable) to the crucial intermediate 5. Saponification of 5 with lithium hydroxide/water/t-butanol gave the corresponding acid 6 (95%), which was treated without isolation with p-nitrophenol and diisopropyl carbodiimide in pyridine to give the p-nitrophenyl ester 7 (86%). Brief treatment of 7 with formic acid gave the corresponding alcohol 8, which was used directly in the next step, because of its sensitivity to self-condensation. Reaction of crude 8 at 0° C. in acetonitril with first an excess of phosphorous oxychloride and triethylamine, then water gave the desired monophosphate 9 in 22% yield from 7, after HPLC purification. Compound 9 gave the expected NMR and LC-MS spectra, and was stable in aqueous solution at acidic pH (0.1% TFA). For convenient storage, however, the material was kept as a DMSO stock solution in the freezer.

Scheme 3, reagents, conditions, and yields:

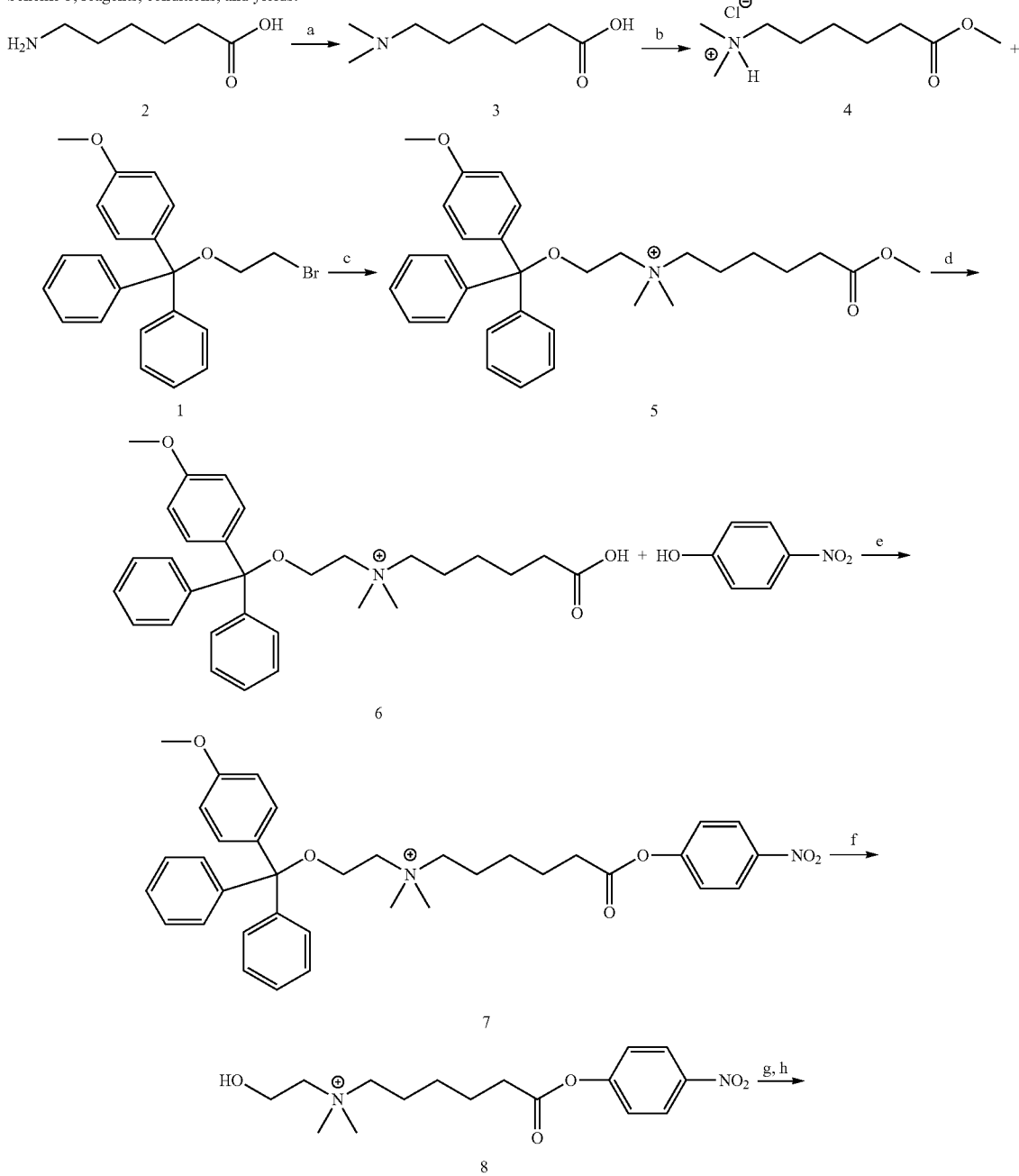

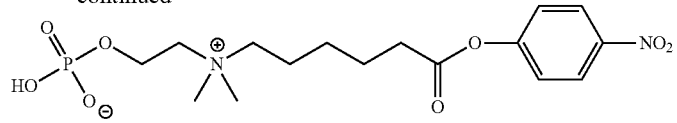

a: CH₂O, H₂, Pd/C (86%);
b: CH₃OH, HCl (96%);
c: Na₂CO₃, CH₃CN (73%);
d: LiOH, t-BuOH/H₂O (95%);
e: DIPCDI, pyridine (86%);
f: HCOOH/H₂O;
g: POCl₃, TEA; h: H₂O (22% from 7).

General methods—Concentrations were performed at reduced pressure (bath temperature <40° C.). NMR spectra were recorded at 298° K with a Varian Unity 500 MHz spectrometer. Only selected NMR data are reported. Assignments were corroborated by appropriate 2-D experiments. Electrospray mass spectroscopy (ES-MS) for dilute methanol or acetonitril solutions was performed in the direct-inlet mode using a Perkin-Elmer SCIEX API 150-EX mass spectrometer. The positive-ion mode spectra were recorded and processed using the manufacturer software on an Apple Macintosh Quadra computer.

TLC was performed on Silica Gel F254 (Merck, Darmstadt, Germany) plates with detection by UV-light and/or by staining with either 5% ninhydrin in butanol or 5% sulfuric acid in ethanol. Column chromatography was performed on Matrex silica gel 60 Å (35-70 μm, Amicon) unless otherwise stated. Preparative HPLC was carried out using a Varian HPLC system consisting of a 9012 gradient pump, a 9065 diode array detector, and a PC computer system running the Varian Star HPLC software. Isolute C-18 EC reversed phase silica (40-70 micron particle size) from International Sorbent Technology Ltd (Mid Glamorgan, UK) was packed and eluted with the specified solvents in open glass columns. Other reagents and solvents were purchased with high commercial quality and were used without further purification unless otherwise stated.

2-Monomethoxytrityloxy-1-bromoethartol (1)—This compound was prepared analogously to the corresponding trityl derivative[13]. Briefly, monomethoxytrityl chloride (3.09 g, 10 mmol) was added to a solution of bromoethanol (1.0 g, 8.0 mmol) in dry pyridine (5 mL) at room temperature. After 12 hrs, TLC (hexane-ethyl acetate, 9:1) indicated presence of two UV-absorbing spots, one (major) with rf 0.9, one (minor) with rf 0.7. Water (0.1 mL) was added, and after 15 min stirring at r.t. the mixture was partitioned between ethyl acetate and aq 2M sulfuric acid, the organic layer was washed with aq. sodium bicarbonate and concentrated. The residue was purified by column chromatography on silica gel (160 g) packed in pentane-ethyl acetate 95:5 and eluted with a pentane-ethyl acetate 95:5-90:10 stepwise gradient. Collection of the main band gave 1 as a syrup (2.75 g, 87%), which crystallized on standing. Alternatively, chromatography could be omitted and the crude syrup crystallized directly from methanol to give pure crystals in a yield of 40-50%. Direct-inlet ES-MS showed a large peak at m/z 273 (monomethoxytrityl cation) but only two very small peaks at 419/421 (M+Na). H-NMR data (CDCl₃): 3.44/3.48 (2 multipets, 2+2H, OCH2CH2Br), 3.83 (s, 3H, ArOCH3), 6.88 (d, 2H, ArH), 7.24-7.52 (m, 12H, Ar—H).

6-(N,N-Dimethylamino)-N-[2-(monomethoxytrityloxy)-ethyl]-hexanoic acid methyl ester (5)—

A solution of 6-aminohexanoic acid (2, 13.2 g) in aqueous formaldehyde (37%, 40 mL) was mixed with Pd/C (1.0 g) and the mixture was hydrogenated in a Parr stainless steel apparatus with magnetic stirring overnight at room temperature and 50 bar. A check by TLC (ethyl acetate-methanol-acetic acid-water, 6:3:3:2, ninhydrin detection) revealed almost complete conversion from starting material (rf 0.7) to a slower-migrating product (rf 0.5, browner color). The reaction mixture was filtered through a bed of Celite, the filter bed was washed with water (20 mL), diluted (60 mL), and the solution was slowly passed through a column of Dowex-50 Wx2-100 mesh (H+ form, 0.7 meq/mL, 150 mL, carefully pre-washed with milli-Q water). The column was then washed with milli-Q water (200+100 mL), and then the product was eluted with 2% aq ammonia (400 mL) The eluate was monitored by TLC (ethyl acetate-methanol-acetic acid-water, 6:3:3:2, ninhydrin detection). The appropriate fractions were partially evaporated, then lyophilized to leave a semi-solid residue (13.7 g, 86%). Direct inlet ES-MS revealed a strong peak at m/z 160.2 (M+H), corresponding to the N,N-dimethylated product (3).

A fraction of this crude material (3.97 g, 25 mmol) in methanol (75 mL) was cooled in ice and stirred while thionyl chloride (10 mL, 134 mmol) was added dropwise during 30 min, after which the cooling was removed and the mixture was left at room temperature overnight. A check by TLC (ethyl acetate-methanol-acetic acid-water, 10:3:3:2, ninhydrin detection) revealed conversion to a slightly faster-moving compound with weaker staining and a different tint. There were also minor faster-moving impurities carrying over from the previous step. After 16 hrs, the reaction mixture was concentrated and co-concentrated several times with methanol to give a residue (5.05 g) which crystallized partially on standing. Direct-inlet ES-MS of this material revealed a strong peak at m/z 174.0 (M+H), corresponding to 6-(N,N-dimethylamino)-hexanoic acid methyl ester (4).

A fraction of this crude material (1.12 g, purity approximately 75%, 4.0 mmol), dry acetonitril (25 mL), 2-(monomethoxytrityloxy)-2-bromoethanol (1, 1.60 g, 4.0 mmol), and solid anhydrous sodium carbonate (800 mg) was refluxed (bath temp 70° C.) overnight, after which TLC showed only partial conversion, so more 1 (800 mg, 2.0 mmol) and sodium carbonate (500 mg) was added, and reflux was continued for another 24 hrs. TLC then showed that the majority of starting material had disappeared, and that there was a new, faster-migrating, ninhydrin-staining and UV-absorbing spot. The mixture was partitioned between dichloromethane and water (the desired material was in the organic phase), the aq. phase was washed with a little dichloromethane, and the combined organic layers were washed with a little water, then concentrated to a small volume (10 mL), which was partitioned between methyl-t-butyl ether and water (the desired material was now in the aqueous phase).

The organic phase was washed with a little water, and the combined aqueous layer was washed with a little methyl-t-butyl ether. The combined aqueous solution was rotavapored shortly to remove non-aqueous solvents (approx. ⅓ of volume was removed) and the residual solution was passed through a Bond-Elut C-18-EC column (35 g, packed in methanol and then equilibrated with water), washed after with water, eluted with first 20%, 50 and then finally 60% methanol in water. The desired material eluted as a pure band with the 60% methanol eluent. Appropriate fractions were collected, a few drops of pyridine were added, and the solution was lyophilized, leaving behind compound 5 as a white solid (1.53 g, 73%). ES-MS showed a strong m/z 490 peak (M+). H-NMR data (CDCl3): 1.31 (m, 2H, H-4), 1.65 (m, 2H, H-3), 1.75 (m, 2H, H-5), 2.31 (t, 2H, H-2), 3.30 (s, 6H, $(CH_3)_2N$), 3.47 (m, 2H, H-6), 3.62 (m, 2H, OCH2CH2N), 3.68 (s, 3H, COOCH3), 3.82 (s, 3H, ArOCH3), 3.93 (m, 2H, OCH2CH2N), 6.89 (d, 2H, ArH), 7.24-7.41 (m, 12H, ArH).

6-(N,N-Dimethylamino)-N-[2-(monomethoxytrityloxy)-ethyl]-hexanoic acid p-nitrophenyl ester (7) A solution of compound 5 (420 mg, 0.86 mmol) in 2:1-butanol-water (6.0 mL) was mixed with lithium hydroxide (72 mg) and the solution was stirred at room temperature for 3 h, after which TLC (ethyl acetate-methanol-acetic acid-water, 12:3:3:2) showed complete conversion into a compound with a slightly lower rf., An ES-MS spectrum at this stage showed m/z 476.0 and 482.3 peaks (M+H and M+Li, respectively). The mixture was diluted with water (10 mL), the pH was adjusted to 7.5 with aq 0.1 M hydrochloric acid, and then the solution was lyophilized to give crude 6 (510 mg, contaminated with lithium chloride). This material (approximately 0.86 mmol) was dissolved in in dry pyridine (6.0 mL), and then p-nitrophenol (400 mg, 2.86 mmol), and diisopropylcarbodiimide (270 microL, 0.176 mmol) was added. After stirring for 3 hrs at RT another portion of diisopropyl carbodiimide (200 microL) was added, and the mixture was stirred for another 24 hrs at r.t., after which TLC (ethyl acetate-methanol-acetic acid-water, 15:3:3:2) indicated complete reaction. The mixture was evaporated and coevaporated ×3 with dichloromethane-toluene to remove pyridine. The residue was partitioned between aqueous 0.2 M triethylammonium acetate (pH 5.0) and methyl t-butyl ether (about 100 mL of each solvent and heavy shaking was necessary to dissolve everything), TLC (ethyl acetate-methanol-acetic acid-water, 10:3:3:2, UV and ninhydrin detection) showed that the product was exclusively in the aq. phase, whereas most of the p-nitrophenol and also other UV-absorbing impurities were in the organic phase. The organic phase was washed with a little aq. buffer, and the combined aqueous phases were washed with methyl t-butyl ether, then extracted with dichloromethane (TLC now indicated complete transfer of product into the organic phase). The aqueous layer was washed with a little dichloromethane, and the combined organic layers were washed with a small amount of buffer, and carefully separated. At this, TLC revealed presence of a very pure material, and H-NMR also confirmed this. The material was kept in the freezer in solution, but could, if necessary, be concentrated to give syrupy, crude 7 (440 mg, 86%). In this faun, the material also remain unchanged for weeks at freezer temperature. An ES-MS of the material showed a strong signal at m/z 596.8 (M+).

H-NMR data (CDCl$_3$): 1.41 (m, 2H, H-4), 1.75-1.85 (m, 4H, H-3, H-5), 2.63 (t, 2H, H-2), 3.24 (s, 6H, $(CH_3)_2N$), 3.49 (m, 2H, H-6), 3.62 (m, 2H, OCH2CH2N), 3.81 (s, 31-1, ArOCH3), 3.84 (m, 2H, OCH2CH2N), 6.89 (d, 2H, ArH), 7.24-7.41 (m, 12H, ArH), 8.28 (d, 2H, ArR).

6-(N,N-Dimethylamino)-N-[(2-phosphoryloxy)-ethyl]-hexanoic acid p-nitrophenyl ester (9)—A solution of compound 7 (55 mg, 0.10 mmol) was dissolved in formic acid (2 mL) and kept at RT for 60 min, then it was concentrated and co-concentrated ×3 with dry acetonitril. The residual compound 8, showing a reasonable purity by TLC (ethyl acetate-methanol-acetic acid-water, 6:3:3:2, ninhydrin and UV detection) and ES-MS (m/z 325.2, M+), was dissolved in dry acetonitril (0.5 mL) and added to a cooled (0° C.) solution of phosphorous oxychloride (0.019 mL, 0.2 mmol, freshly distilled) and triethylamine (0.069 mL, 0.5 mmol) in dry acetonitril (0.5 mL). After 1 h at 0° C., more phosphorous oxychloride (0.05 mL) and triethylamine (0.05 mL) was added, and after another hour water (0.05 mL) was added and the mixture was further stirred at 0° C. for 1 hour, after which TLC showed disappearance of most starting material, and appearance of a UV-absorbing spot with very low (rf 0.05) mobility. The reaction mixture was diluted with 0.2% aq TFA (3.8 mL), washed with methyl t-butylether (3.5 mL), the aq phase was carefully separated, rotavapored shortly at 35° C. (down to approx. ⅔ volume) and the resulting solution was injected in 400 microL portions on a Supelco Discovery C-18 column (15×21.2 cm, 5 microM), using a flow of 8.0 mL/min and a gradient over 40 min from 82% to 58% water in acetonitril (a 0.1% TFA concentration was maintained throughout). One major and one minor UV-absorbing (300 nm) peak were seen at 18-20 min and 24-26 min respectively, corresponding to desired product 9 and starting material 8, respectively. Fractions containing 9 were pooled, concentrated to a small volume, and lyophilized to give pure 9 as an amorphous material (9 mg, 22% from 7). An LC-MS spectrum showed a dominating m/z 405.2 signal (M+). H-NMR data (DMSO-d6): 1.38 (m, 2H, H-4), 1.67-1.78 (m, 4H, H-3, H-5), 2.69 (t, 2H, H-2), 3.01 (s, 6H, $(CH3)_2N$), 3.35 (m, 2H, H-6), 3.60 (m, 2H, OCH2CH2N), 4.24 (m, 2H, OCH2CH2N), 7.44 (d, 2H, ArH), 8.31 (d, 2H, ArH). H-NMR data (D2O, HOD=4.68): 1.35 (m, 2H, H-4), 1.66 (m, 2H, H-3 or H-5), 1.72 (m, 2H, H-3 or H-5), 2.59 (t, 2H, H-2), 3.02 (s, 6H, (CH3)2N), 3.28 (m, 2H, H-6), 3.52 (m, 2H, OCH2CH2N), 4.19 (m, 2H, OCH2CH2N), 7.22 (d, 2H, ArH), 8.19 (d, 2H, ArH).

Peptide Synthesis

Figure 1:
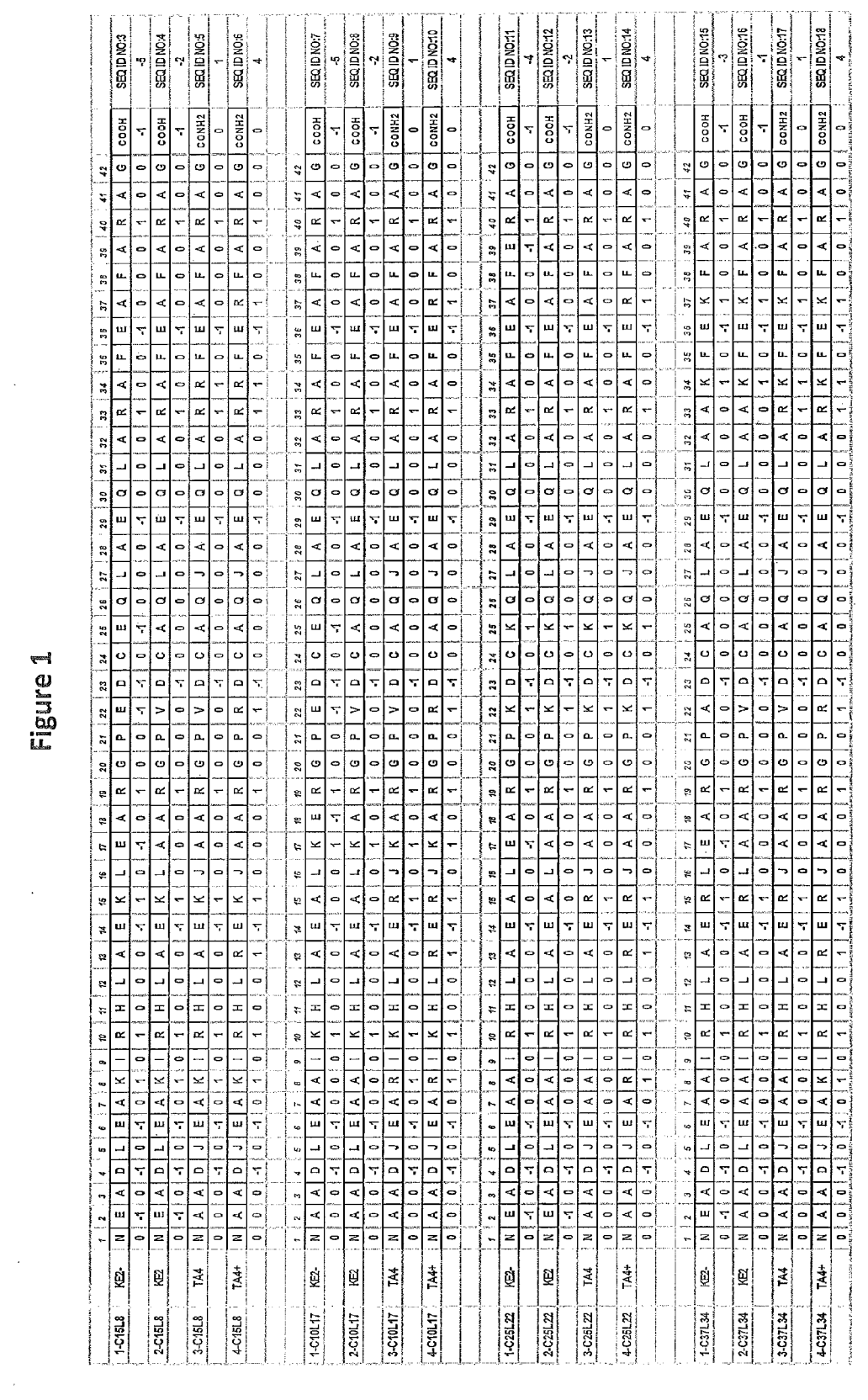

A library of sixteen 42-residue peptides (FIG. 1) was prepared by solid-phase peptide synthesis. The components of the library varied with regards to the number of charged residues and the position of incorporation of the ligand. The synthesis procedure was the same in each case and is exemplified here by that of 3-C15L8Cys24 (TA4Cys(Acm)).

The polypeptide was synthesized on a Pioneer automated peptide synthesizer (Applied Biosystems) using standard Fmoc chemistry. The synthesis was performed on 0.1 mmol scale on Fmoc-PAL-PEG-PS resin with a substitution level of 0.2 mmol/g. The following amino acid derivatives (Novabiochem AG) were used: Fmoc-Ala-OH, Fmoc-Arg(Pbf)-OH, Fmoc-Asn(Trt)-OH, Fmoc-Asp(tBu)-OH, Fmoc-Cys(Acm)-OH, Fmoc-Gln(Trt)-OH, Fmoc-Glu(tBu)-OH, Fmoc-Gly-OH, Fmoc-His(Trt)-OH, Fmoc-Ile-OH, Fmoc-Leu-OH, Fmoc-Lys(Aloc)-OH, Fmoc-Lys(Boc)-OH, Fmoc-Nle-OH, Fmoc-Phe-OH, Fmoc-Pro-OH, Fmoc-Val-OH. The side chain of Lys 15 was Aloe protected, whereas Boc protection was used for Lys 8. A fourfold excess of amino acid derivative was used for each coupling step. TBTU (O-(7-benzotriazole-1-yl)-1,1,3,3-tetramethyluronium tetrafluoroborate, 0.5M in DMF) was used as coupling reagent in combination with DIEA (diisopropyl ethyl amine, 1M in DMF). A standard coupling time of 60 min was used, except for Gln, Cys, Pro and His (90 min) and the first residue, Arg, and Asn (2 h). After the conventional automated solid phase peptide synthesis was completed, the free N-terminus was acetylated with acetic anhydride treating the resin for 2 h with a mixture of acetic anhydride/dichloromethane (3:1) and the resin was washed with dichloromethane (6×) and shrunk with diethyl ether. The Aloe protecting group was removed with 3 eq. of tetrakis(triphenyl)palladium(0) in chloroform/acetic acid/ NMM (N-methyl morpholine (18:2:1) for 2.5 h. The resin was consecutively washed with DIEA (0.5% in DMF), sodium diethyl dithiocarbamic acid (0.5% in DMF), dichloromethane and shrunk with diethyl ether, 7-methoxycoumarin-3-carboxylic acid (3 eq.) was coupled to the side chain of Lys 15 with HBTU (3 eq.), HOBt (3 eq.) and DIEA (6 eq.) in DMF for 4 h. The resin was washed with DMF, dichloromethane and shrunk with diethyl ether. The peptide was cleaved from the resin with TFA, TIS (triisopropyl silane) and water (95:2.5:2.5, 1 ml per 100 mg of resin) over 2 h at room temperature. The TFA was evaporated under reduced pressure and the peptide was precipitated by addition of cold diethyl ether, centrifuged, washed and lyophilized. The crude product was purified by RP HPLC (Hichrom C8, 21.2 mm×25 cm, 10 μm, A: 0.1% TFA, 10% ACN in $H_2O$, B: 0.1% TFA 10% $H_2O$ in ACN, 38 to 46% B over 18 min, $t_R$=16.0 min).

Preparation of Peptide Scaffold Dimers.

Disulfide bond formation (H. Tamamura, A. Otaka, J. Nakamura, K. Okubo, T. Koide, K. Ikeda, T. Ibuka, N. Fuji *Int. J. Peptide Protein Res.* 1995, 45, 312-319.):

The peptide (2.4 mg (0.51 μmol) of 3-C15L8Cys(Acm)24) was dissolved in TFA (200 μl) and silver triflate (5 mg, 20 μmol) and anisole (1 drop) were added. The reaction mixture was incubated in the refrigerator at 4° C. for 24 h. After addition of diethyl ether the peptide precipitated and was washed 3 times with cold diethyl ether. To the precipitate were added DMSO (0.25 ml) and 1 N HCl (1 ml). The reaction mixture was stirred at room temperature for 22 h. The suspension was centrifuged and the precipitate was discarded. The liquid was neutralized with diluted NaOH and analyzed by RP-HPLC (analytical run: Varian C18, 150×4.6 mm, 5 μm, A: 0.1% TFA, 10% ACN in $H_2O$, B: 0.1% TFA 10% $H_2O$ in ACN, 30 to 60% B over 30 min, $t_R$=23.4 min.

Reaction of $PC_6$-pNitrophenylester with $TA_4^+Cys(Acm)$.

This is a specific example of a protocol for incorporating a phosphocholine derivative into a peptide, in this case $TA_4+$ with a protective group Acm on the Cys-residues.

To a solution of $TA_4^+Cys(Acm)$ peptide (500 μg, 0.1 μmole) in 100 μL of 0.1 M phosphate buffer pH8 were added 2.8 μL of 0.1 M PC6-pNitrophenylester in DMSO (0.3 μmole, 3 eq.). The reaction mixture was incubated at 4° C. LC-MS (Phenomenex Gemini, C18, 5 μm, 150×3.0 mm, A: 0.1% formic acid in water, B: 0.1% formic acid in acetonitrile, 10-90% B over 10 min) $t_R$=4.1 min (UV signal), m/z=670.5 for $[M+8H]^{8+}$, 766.1 for $[M+7H]^{7+}$, 893.3 for $[M+6H]^{6+}$, 1071.9 for $[M+5H]^{5+}$.

Immobilization of TA4+PC6Cys(Acm) Peptide on Porous Polystyrene Coated with F108-2-Pyridyl Disulfide To a solution of $TA_4^+PC6Cys(Acm)$ peptide (90 μg, 18 nmol) in 18 μL of 0.1 M phosphate buffer pH 8 were added 1.8 μL of 5 mg/mL iodine in 50% MeOH in water (8.6 μg, 34 nmol, 2-fold excess relative to thiol groups). The reaction mixture was incubated at 25° C. for 20 min, cleaned with PepClean C18 Columns (Pierce) and added directly to a 50 μL suspension containing 10 mg of F108-PDS-coated porous particles in phosphate buffer.

Kinase-Peptide Conjugation

To a solution of $TA_4^+PC6Cys(Acm)$ peptide (90 μg, 18 nmol) in 18 μL of 0.1 M phosphate buffer pH 8 were added 1.8 μL of 5 μg/mL iodine in 50% MeOH in water (8.6 μg, 34 nmol, 2-fold excess relative to thiol groups). The reaction mixture was incubated at 25° C. for 20 min, cleaned with PepClean C18 Columns (Pierce) and added directly to a 1.5 mL of 1.3 mg/ml Kinase-PDS in phosphate buffer.

Formation of $TA_4PC6CysH$

Reaction of $PC_6$-pNitrophenylester with $TA_4Cys(Acm)$. To a solution of $TA_4Cys(Acm)$ peptide (1 mg, 0.2 μmol) in 1 mL of 0.1 M phosphate buffer pH8 were added 10 μL of 0.1 M PC6-pNitrophenylester in DMSO (0.8 μmol, 5 eq.). The reaction mixture was incubated at 4° C. for 2 days, purified by gel filtration using NAP-10 columns (GE Healthcare) to have 1.5 mL of $TA_4PC6Cys(Acm)$ in water and finally lyophilized. LC-MS (Phenomenex Gemini, C18, 5 μm, 150×3.0 mm, A: 0.1% formic acid in water, B: 0.1% formic acid in acetonitrile, 10-90% B over 10 min) $t_R$=4.1 min (UV signal), m/z=856.0 for $[M+6H]^{6+}$, 1026.8 for $[M+5H]^{5+}$, 1282.6 for $[M+4H]^{4+}$.

Cysteine deprotection. $TA_4PC6Cys(Acm)$ was dissolved in 1 mL of TFA/anisole (99:1) and 6 mg of AgOTf were added (20 μmol, 100 eq.). After 2 hours at 4° C., the peptide silver salt was precipitated with cold ether, isolated by centrifugation and washed 2 times with ether. 116 μL of 10 mg/ml. DTT in 1 M acetic acid were added and the solution volume was extended to 1 mL with 1 M acetic acid. After one night at 25° C. the peptide was purified by gel filtration using NAP-15 columns to have 1.5 mL of TA4PC6CysH in water and lyophilized. LC-MS (Phenomenex Gemini, C18, 5 μm, 150×3.0 mm, A: 0.1% formic acid in water, B: 0.1% formic acid in acetonitrile, 10-90% B over 10 min) $t_R$=4.6 min (UV signal), m/z=843.5 for $[M+6H]^{6+}$, 1012.3 for $[M+5H]^{6+}$, 1264.6 for $[M+4H]^{4+}$.

Formation of $TA_4^+PC6CysH$

Reaction of $PC_6$-pNitrophenylester with $TA_4^+Cys(Acm)$. To a solution of $TA_4^+Cys(Acm)$ peptide (1 mg, 0.2 μmol) in 1 mL of 0.1 M phosphate buffer pH8 were added 10 μL of 0.1 M PC6-pNitrophenylester in DMSO (0.8 μmol, 5 eq.). The reaction mixture was incubated at 4° C. for overnight, purified by gel filtration using NAP-10 columns (GE Healthcare) to have 1.5 mL of $TA_4^+PC6Cys(Acm)$ in water and finally lyophilized. LC-MS (Phenomenex Gemini, C18, 5 μm, 150×3.0 mm, A: 0.1% formic acid in water, B: 0.1% formic acid in acetonitrile, 10-90% B over 10 min) $t_R$=4.0 min (UV signal), m/z=670.3 for $[M+8H]^{8+}$, 766.1 for $[M+7H]^{7+}$, 893.4 for $[M+6H]^{6+}$.

Cysteine deprotection. $TA_4^+PC6Cys(Acm)$ was dissolved in 1 mL of TFA/anisole (99:1) and 6 mg of AgOTf were added (20 μmol, 100 eq.). After 2 hours at 4° C., the peptide silver salt was precipitated with cold ether, isolated by centrifugation and washed 2 times with ether. 116 μL of 10 mg/ml DTT in 1 M acetic acid were added and the solution volume was extended to 1 mL with 1 M acetic acid. After one night at 25° C. the peptide was purified by gel filtration using NAP-15 columns to have 1.5 mL of $TA_4^+PC_6CysH$ in water and lyophilized. LC-MS (Phenomenex Gemini, C18, 5 μm, 150×3.0 mm, A: 0.1% formic acid in water, B: 0.1% formic acid in acetonitrile, 10-90% B over 10 min) $t_R$=4.6 min (UV signal), m/z=661.5 for $[M+8H]^{8+}$, 755.9 for $[M+7H]^{7+}$, 881.6 for $[M+6H]^{6+}$.

Incorporation of Ligand into Each Polypeptide Scaffold of the Peptide Library.

A more general protocol for incorporation of a phosphocholine derivative is given below. A person skilled in the art will be able to adapt this protocol in order to optimize it for specific conditions that may apply.

Each peptide from the library is dissolved in 1 mL 50 mM phosphate buffer, pH 8, to a concentration of 1 mM to form a stock solution. The amount of peptide needed to form the stock solution is calculated from its molecular weight assuming a water content of 25%. The concentration of each stock solution is determined using an extinction coefficient of 20300 M$^{-1}$ cm$^{-1}$ at 355 nm. 100 μL of each stock solution is transferred to a well of a microtitre plate and two eq. of the active ester of the ligand to be tested dissolved in DMSO at an initial concentration of 100 mM is added and left to react for 1 hr.

Affinity Measurements

In a separate set of wells of the microtitre plate the C-reactive protein (CRP) was dissolved to a concentration of 500 nM in 10 mM HEPES, 150 mM NaCl and 5 mM CaCl$_2$ at pH 7.4. Each one of the polypeptides functionalized with ligand and fluorophore was diluted and added to each well containing the target protein, to give a final concentration of peptide of 500 nM.

As a negative control, in a parallel experiment the same procedure was applied using polypeptides with fluorophore but without ligand. The microtitre plate was introduced into a fluorescence based plate reader set for excitation at 355 nm and emission at 420 nm. Peptides for which the fluorescence emission was different between polypeptide functionalized with ligand and polypeptide without ligand were considered as "hits" and selected for more careful analysis.

An experimental protocol for careful analysis of affinity using a fluorimeter is given in Table I and FIG. 2. The polypeptide used has the sequence named 3-C15L8. Although the analysis of the fluorescent data is complicated by the fact that C-reactive protein has five binding sites for phosphocholine it is clear that the affinity for the functionalized polypeptide in the presence of 5 mM CaCl$_2$ is compatible with a dissociation constant of low nM or better.

The corresponding experiment with the polypeptide carrying fluorophore but no ligand showed no change in fluorescence as a function of the concentration of CRP, showing that the polypeptide scaffold itself has very low affinity for CRP. Consequently, the combination of polypeptide and phosphocholine derivative forms a binder for CRP where cooperative interactions between the components of the functionalized polypeptide and CRP gives rise to a very high overall affinity.

Solid Phase CRP Detection Assay

Figure 3:
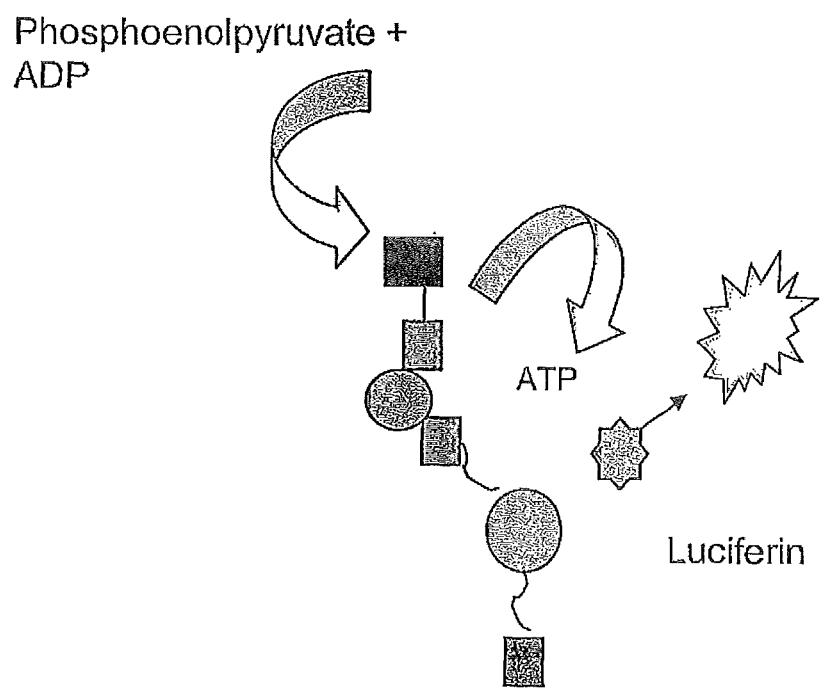
FIG. 3 is a schematic view of a CRP detection assay using the CRP-binder of the present invention.

One embodiment of a CRP detection assay having the binder of the present invention bound to a solid phase is schematically shown in FIG. 3. In this assay the capture of CRP is accomplished by a CRP-binder attached to latex particles and the recognition signal is generated by the binder conjugated to the enzyme pyruvate kinase. The kinase phosphorylates ADP, with the help of added PEP (phosphoenolpyruvate), to foul). ATP. The ATP, in turn, forms a complex with the enzyme luciferase which enables it to catalyze the oxidation of luciferin to oxyluciferin. This reaction generates light. The light intensity becomes a direct measure of the amount of kinase in the sample, which in turn is a measure of the amount of CRP bound, Preparation of CRP-Binders Bound to Latex Particles Monodisperse polystyrene latex particles with a diameter of 239 nm were suspended in ultra-pure (MilliQ) water containing the polymeric surfactant Pluronic F108, containing pyridyl disulfide (PDS) conjugated end-groups to allow linking of thiol containing ligands. The surfactant molecules adsorb to the particles via their hydrophobic center blocks[14]. The number of Pluronic molecules taken up, through overnight adsorption, by each particle was determined by sedimentation field-flow fractionation, SdFFF to be 16500[15]. The PDS groups were then replaced by either the Cys-containing CRP-binder. A protocol for immobilising a binder (Ta4+) is given above. The analysis by SdFFF indicated that each particle had taken up 2560 binders.

The enzyme pyruvate kinase (type III from Rabbit muscle; Sigma-Aldrich product nr. P9136-5KU) was assayed, either as received, or after treatment with the bifunctional linker molecule, SPDP (Pierce Biotechnology, product nr. 21857), or after attachment to the binder via a disulfide bridge (exemplary protocol given above). The three forms of the enzyme were assayed for their respective ability to phosphorylate ADP in the following manner: aliquots containing 0.36 mg kinase in 50 mM glycine-TRIS buffer of pH 7.6 were each added to the "luminescence reagent", i.e. a mixture of 40 μL

TABLE 1

Figure 4:
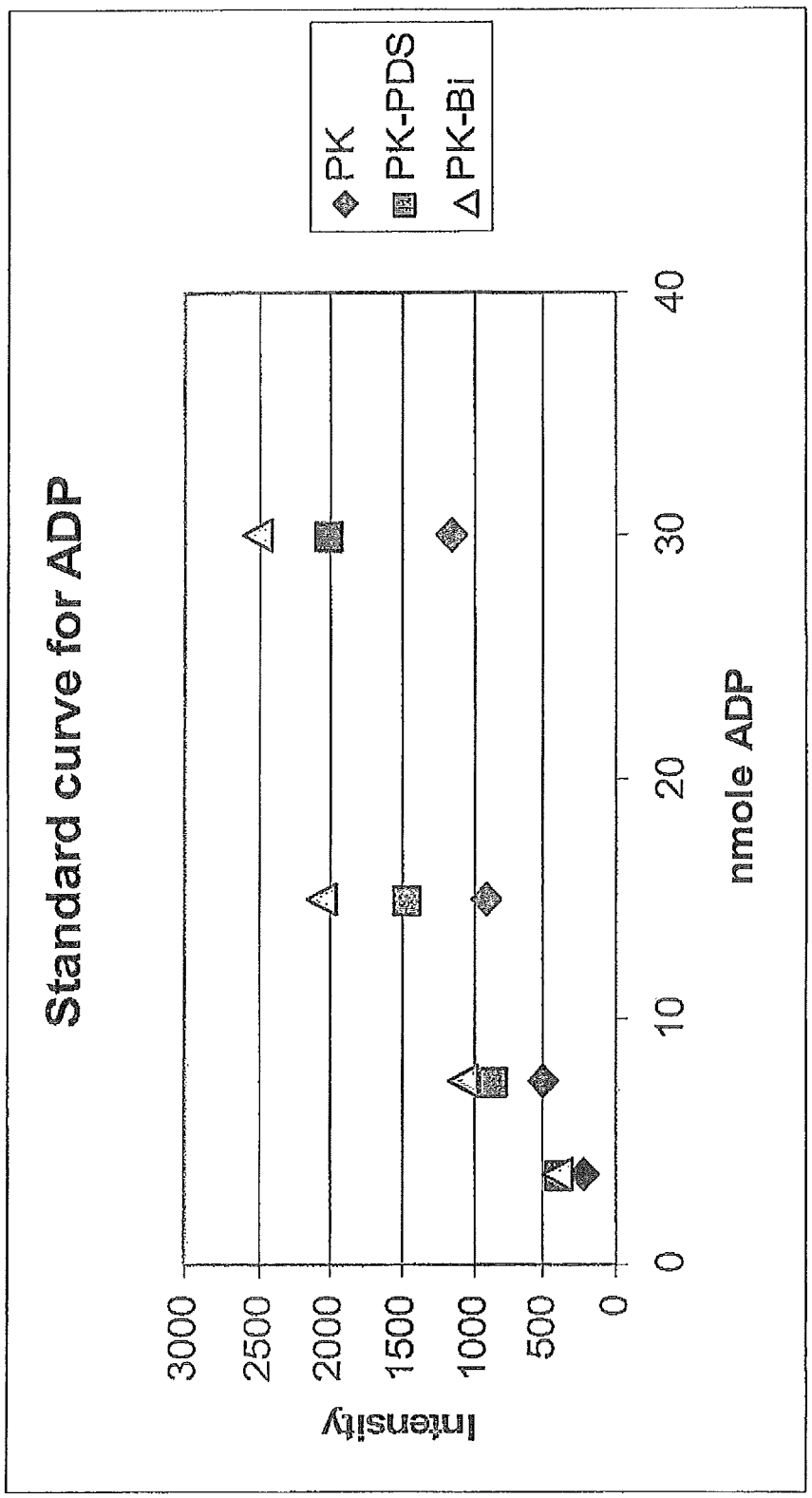
FIG. 4 shows the activity of native pyruvate kinase, pyruvate kinase bound to a linker, and pyruvate kinase bound to a CRP-binder, respectively.

| Peptide | Buffer | Conc peptide (nM) | Conc CRP (nM) | Vol CRP | Vol peptide | Vol buffer | Intensities | | | Average | Error |
|---|---|---|---|---|---|---|---|---|---|---|---|
| 4-C15L8-PC6 | Bis Tris 20 mM, 5 mM CaCl2 pH 7.2 | 100 | 0 | 0 | 10 | 490 | 456.78 | 486.4 | 527.63 | 490.27 | 35.58319 |
| | | 100 | 5 | 0.5 | 10 | 489.5 | 449.62 | 477.97 | 489.83 | 472.4733 | 20.66086 |
| | | 100 | 10 | 1 | 10 | 489 | 456.17 | 455.1 | 450.21 | 453.8267 | 3.177489 |
| | | 100 | 25 | 2.5 | 10 | 487.5 | 446.88 | 433.51 | 446.39 | 442.26 | 7.581682 |
| | | 100 | 50 | 5 | 10 | 485 | 423.14 | 393.56 | 409.77 | 408.8233 | 14.81271 |
| | | 100 | 75 | 7.5 | 10 | 482.5 | 406.08 | 365.75 | 408.88 | 393.57 | 24.13347 |
| | | 100 | 100 | 10 | 10 | 480 | 399.31 | 381.79 | | 390.55 | 12.38851 |
| | | 100 | 150 | 15 | 10 | 475 | 413.76 | 389.49 | | 401.625 | 17.16148 |
| | | 100 | 200 | 20 | 10 | 470 | 405.77 | | | 405.77 | |
| 4-C15L8 | Bis Tris 20 mM, 5 mM CaCl2 pH 7.2 | 100 | 0 | 0 | 10 | 490 | | | | | |
| | | 100 | 5 | 0.5 | 10 | 489.5 | | | | | |
| | | 100 | 10 | 1 | 10 | 489 | | | | | |
| | | 100 | 25 | 2.5 | 10 | 487.5 | | | | | |
| | | 100 | 50 | 5 | 10 | 485 | | | | | |
| | | 100 | 75 | 7.5 | 10 | 482.5 | | | | | |
| | | 100 | 100 | 10 | 10 | 480 | | | | | |
| | | 100 | 150 | 15 | 10 | 475 | | | | | |
| | | 100 | 200 | 20 | 10 | 470 | | | | | |
| — | Bis Tris 20 mM, 5 mM CaCl2 pH 7.2 | 0 | 0 | 0 | 0 | 500 | | | | | |
| — | Bis Tris 20 mM, 5 mM CaCl2 pH 7.2 | 0 | 1500 | 15 | 0 | 485 | | | | | | luciferase ("Thermostable", from BioThema AB, Stockholm) at 0.5 mg/mL, 10 μL PEP (Sigma-Aldrich) at 8.9 mg/mL, 10 μL 15 mM luciferin (Sigma-Aldrich). At time t=zero aliquots of 10 μL ADP (Sigma-Aldrich, 2.6 mg/mL) were added to each sample mixture and the light emission was followed with a CCD camera for 300 sec. The results are shown in FIG. 4. The three forms were largely of comparable activity. The commercial product was unexpectedly somewhat less active than its modified forms, probably caused by an (unintended) removal of some minor inhibitor during the processing.

Figure 5:
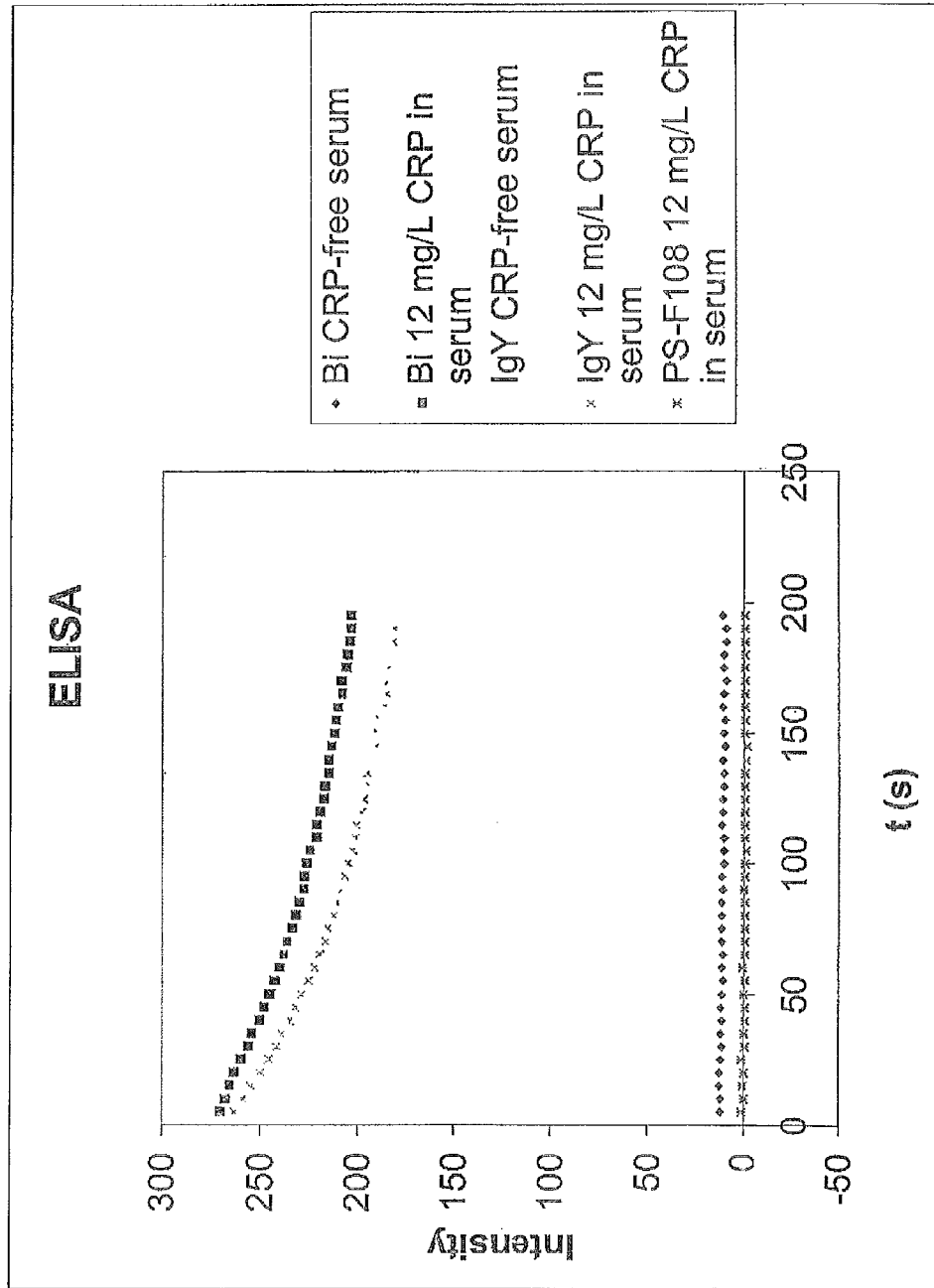
FIG. 5 is a comparison of signals generated by kinase-bound CRP-binder of the present invention and kinase-bound CRP-specific antibody, respectively.

The photon flux was measured by a CCD camera from a reaction mixture of the type illustrated in FIG. 3 and, for comparison, from a reaction mixture having an CRP-specific IgY antibody as CRP-binding agent instead of the CRP-binder of the present invention. The reagent concentrations and total amounts were the same as described for the "luminescence reagent" in FIG. 4. The samples were either CRP-free serum or serum containing 12 mg CRP/L. The highest photon flux was that provided by a mixture wherein CRP-binders on the particle surfaces had captured CRP from the concentrated serum sample. After 3 cycles of washing and centrifugation the composite sample was allowed to take up binder-kinase conjugate; it was then mixed with the above luminescence reagent and allowed to generate its photon flux. Similarly, particles containing antibodies (IgY anti-CRP, a gift from Prof. A. Larsson, Uppsala Academic Hospital) were allowed to bind CRP from the serum of known (12 mg/L) concentration. An antibody-kinase conjugate was added to generate the photon flux, as described. The CRP-free serum was used as blank. In addition to the four samples just described, there was one that consisted only of surfactant coated nanoparticles of the same size as those carrying binders or antibodies in the four actual samples. The results are shown in FIG. 5. The figure clearly shows that the binder-based detection of CRP gives a strong signal, while the binder-based signal from CRP-free serum gives a straight baseline of zero light intensity. The antibody-based detection gives a somewhat weaker signal in the CRP-containing serum, but demonstrates a higher non-specific adsorption than the binder-analogue to judge from the signal resulting from the CRP-free serum. The surfactant-coated particles are clear blanks in this study.

Figure 6:
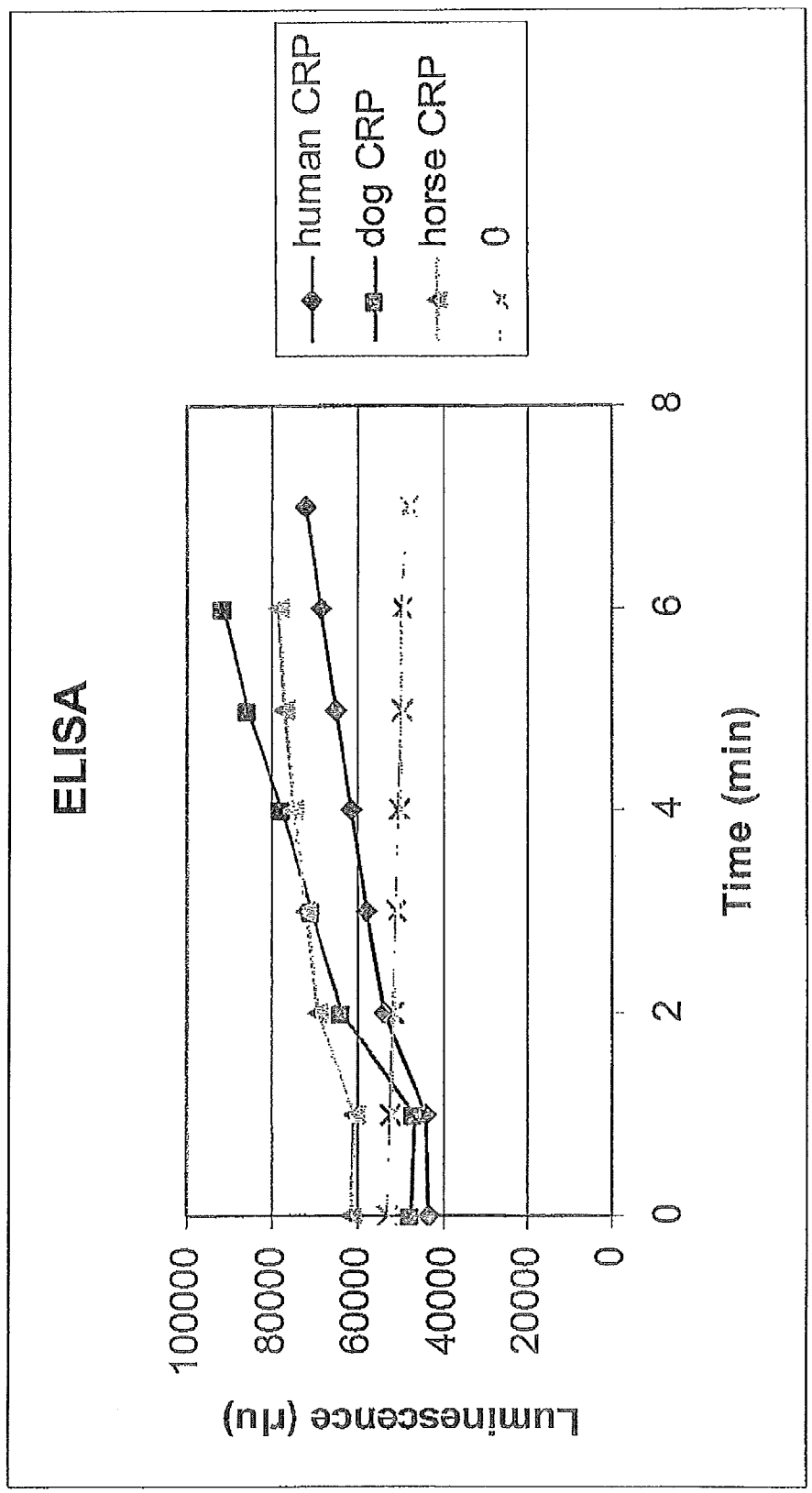
FIG. 6 is a comparison of signals generated by a kinase-bound CRP-binder of the present invention used for detection of CRP from human, horse and dog.

An experiment analogous to that of FIG. 5 was performed on binder-conjugated latex particles (10 μL, 10% w/v polystyrene particles with 239 nm diameter). The particles were added to 100 μL of serum from dog, horse, or human subjects where the former two had unknown contents of CRP and the latter contained 12 mg/L. After 10 minutes of incubation the particles were washed three times with centrifugation and then incubated with binder-kinase conjugate for 15 minutes. After a three-fold wash procedure, and addition of the "luminescence reagent" described under FIG. 4, the samples were scanned by a luminometer from BioThema which measures cumulative photon generation and computes rates of ATP generation as a measure of kinase concentration, in turn proportional to the amount of CRP in the sample. The results are shown in FIG. 6 and Table 1. From this analysis it is clear that the binders have the ability to capture CRP not only from humans, but from dog and horse as well.

TABLE 2

| Sample | Reaction rate (pmol/min) |
| --- | --- |
| Human CRP | 0.045 ± 0.007 |
| Dog CRP | 0.084 ± 0.009 |
| Horse CRP | 0.026 ± 0.007 |

REFERENCES

[1] Hansen, H. J., LaFontaine, G., Newman, E. S., Schwartz, M. K., Malkin, A., Mojzisik, K., Martin, E. W., Goldenberg, D. M., (1989) Solving the problem of antibody interference in commercial "sandwich"-type immunoassays of carcinoembryonic antigen. Clin. Chem., 35, 146-151.

[2] Moseley, K. R., Knapp, R. C., Haisma, H. J., (1988) An assay for the detection of human anti-marine immunoglobulins in the presence of CA125 antigen. J. Immunol. Methods, 106, 1-6.

[3] R. P. Jain, R. M. Williams *Tetrahedron* 2001, 57, 6505-6509.

[4] A. Kamitani, N. Chatani, S. Murai *Angew. Chem.* 2003, 115, 1435-1437; *Angew. Chem. Int. Ed.* 2003, 42, 1397-1399.

[5] S. Kim, J. I. Lee, Y. C. Kim *J. Org. Chem.* 1985, 50, 560-565.

[6] C. E. McKenna, M. T. Higa, N. H. Cheung, M.-C. McKenna *Tetrahedron Lett.* 1977, 18, 155-158. b) C. E. McKenna, J. Schmidhauser *J. Chem. Soc., Chem. Comm.* 1979, 739.

[7] P. A. Bartlett, L. A. McQuaid *J. Am. Chem. Soc.,* 1984, 106, 7854-7860.

[8] W. C. Chan, P. D. White in *Fmoc Solid Phase Peptide Synthesis, A Practical Approach* (Eds.: W. C. Chan, P. D. White) Oxford University Press, Oxford 2000, pp. 55-56.

[9] E. G. Brown, J. M. Nuss *Tetrahedron Lett.* 1997, 38, 8457-8460,

[10] J. Cai, B. Wathey *Tetrahedron Lett.* 2001, 42, 1383-1385.

[11] R. P. Jain, R. M. Williams: Asymmetric synthesis of (S)-(+)-carnitine and analogs, *Tetrahedron* 57 (2001) 6505-09.

[12] S. Rahal, L. Badache: The Eschweiler-Clarke methylation of amino acids, *Journal de la Societe Algerienne de Chimie* 4 (1994), 75-85

[13] P A Fowler, A. H. Haines, R. J. K. Taylor, E. J. T. Chrystal, M. B. Gravestock: Synthesis and biological activity of acyclic analogues of Nojirimycin, *JCS Perkin* 1 (1994) 2229-35.

[14] Bohner, M., Ring, T. A., Rapoport, N. and Caldwell, K. D. "Fibrinogen uptake by PS latex particles coated with various amounts of a PEO/PPO/PEO triblock copolymer", J. Biomaterials Sci., Polymer ed., 13 (2002), 733-746.

[15] Andersson, M., Fromell, K., Gullberg, E., Artursson, P., and Caldwell, K. D. "Characterization of Surface Modified Nanoparticles for in vivo Biointeraction—A Sedimentation Field-Flow Fractionation Study", *Analytical Chemistry* (2005) 77, 5488-5493.

The invention claimed is:

1. An isolated polypeptide comprising an amino acid sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

2. An isolated polypeptide comprising an amino acid sequence having at least 95% identity to an amino acid sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18, wherein said isolated polypeptide has a binding affinity for C-Reactive Protein ("CRP") of about 100-1000 micromolar.

3. An isolated polypeptide comprising an amino acid sequence having at least 98% identity to an amino acid sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18, wherein said isolated polypeptide has a binding affinity for C-Reactive Protein ("CRP") of about 100-1000 micromolar.

4. An isolated polypeptide consisting of an amino acid sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

5. A library of isolated polypeptides comprising the polypeptides of SEQ ID NOs 3-18.

6. A composition comprising an isolated polypeptide according to claim 1, claim 2, claim 3, or claim 4.

7. A composition comprising an isolated polypeptide according to claim 1, claim 2, claim 3, or claim 4 and a pharmaceutically-acceptable carrier.

* * * * *

SEQUENCE LISTING

<160> NUMBER OF SEQ ID NOS: 18

<210> SEQ ID NO 1
<211> LENGTH: 42

```
<212> TYPE: PRT
<213> ORGANISM: Artificial
<220> FEATURE:
<223> OTHER INFORMATION: Scaffold polypeptide
<220> FEATURE:
<221> NAME/KEY: MISC_FEATURE
<222> LOCATION: (2)..(2)
<223> OTHER INFORMATION: Glu or Ala
<220> FEATURE:
<221> NAME/KEY: VARIANT
<222> LOCATION: (5)..(5)
<223> OTHER INFORMATION: Leu or Nle
<220> FEATURE:
<221> NAME/KEY: VARIANT
<222> LOCATION: (8)..(8)
<223> OTHER INFORMATION: Lys, Ala or Arg
<220> FEATURE:
<221> NAME/KEY: VARIANT
<222> LOCATION: (10)..(10)
<223> OTHER INFORMATION: Lys or Arg
<220> FEATURE:
<221> NAME/KEY: VARIANT
<222> LOCATION: (13)..(13)
<223> OTHER INFORMATION: Ala or Arg
<220> FEATURE:
<221> NAME/KEY: VARIANT
<222> LOCATION: (15)..(15)
<223> OTHER INFORMATION: Lys, Ala or Arg
<220> FEATURE:
<221> NAME/KEY: VARIANT
<222> LOCATION: (16)..(16)
<223> OTHER INFORMATION: Leu or Nle
<220> FEATURE:
<221> NAME/KEY: VARIANT
<222> LOCATION: (17)..(17)
<223> OTHER INFORMATION: Glu, Ala or Lys
<220> FEATURE:
<221> NAME/KEY: VARIANT
<222> LOCATION: (22)..(22)
<223> OTHER INFORMATION: Glu, Val, Arg, Ala or Lys
<220> FEATURE:
<221> NAME/KEY: VARIANT
<222> LOCATION: (24)..(24)
<223> OTHER INFORMATION: Ala or Cys
<220> FEATURE:
<221> NAME/KEY: VARIANT
<222> LOCATION: (25)..(25)
<223> OTHER INFORMATION: Glu, Ala or Lys
<220> FEATURE:
<221> NAME/KEY: VARIANT
<222> LOCATION: (27)..(27)
<223> OTHER INFORMATION: Leu or Nle
<220> FEATURE:
<221> NAME/KEY: VARIANT
<222> LOCATION: (33)..(33)
<223> OTHER INFORMATION: Ala or Arg
<220> FEATURE:
<221> NAME/KEY: VARIANT
<222> LOCATION: (34)..(34)
<223> OTHER INFORMATION: Ala, Arg or Lys
<220> FEATURE:
<221> NAME/KEY: VARIANT
<222> LOCATION: (37)..(37)
<223> OTHER INFORMATION: Ala, Arg or Lys

<400> SEQUENCE: 1

Asn Xaa Ala Asp Xaa Glu Ala Xaa Ile Xaa His Leu Xaa Glu Xaa Xaa
1               5                   10                  15

Xaa Glu Arg Gly Pro Xaa Asp Xaa Xaa Gln Xaa Ala Glu Gln Leu Ala
                20                  25                  30

Xaa Xaa Phe Glu Xaa Phe Ala Arg Ala Gly
            35                  40

<210> SEQ ID NO 2
<211> LENGTH: 42
<212> TYPE: PRT
```

-continued

```
<213> ORGANISM: Artificial
<220> FEATURE:
<223> OTHER INFORMATION: Prior art scaffold
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid

<400> SEQUENCE: 2

Asn Ala Ala Asp Leu Glu Ala Xaa Ile Arg His Leu Ala Glu Lys Leu
1               5                   10                  15

Ala Ala Arg Gly Pro Xaa Asp Ala Ala Gln Leu Ala Glu Gln Leu Ala
            20                  25                  30

Xaa Xaa Phe Glu Ala Phe Ala Arg Ala Gly
        35                  40

<210> SEQ ID NO 3
<211> LENGTH: 42
<212> TYPE: PRT
<213> ORGANISM: Artificial
<220> FEATURE:
<223> OTHER INFORMATION: 1-D15L8
<220> FEATURE:
<221> NAME/KEY: MISC_FEATURE
<222> LOCATION: (8)..(8)
<223> OTHER INFORMATION: Ligand attachment site
<220> FEATURE:
<221> NAME/KEY: MISC_FEATURE
<222> LOCATION: (15)..(15)
<223> OTHER INFORMATION: Reporter attachment site

<400> SEQUENCE: 3

Asn Glu Ala Asp Leu Glu Ala Lys Ile Arg His Leu Ala Glu Lys Leu
1               5                   10                  15

Glu Ala Arg Gly Pro Glu Asp Cys Glu Gln Leu Ala Glu Gln Leu Ala
            20                  25                  30

Arg Ala Phe Glu Ala Phe Ala Arg Ala Gly
        35                  40

<210> SEQ ID NO 4
<211> LENGTH: 42
<212> TYPE: PRT
<213> ORGANISM: Artificial
<220> FEATURE:
<223> OTHER INFORMATION: 2-D15L8
<220> FEATURE:
<221> NAME/KEY: MISC_FEATURE
<222> LOCATION: (8)..(8)
<223> OTHER INFORMATION: Ligand attachment site
<220> FEATURE:
<221> NAME/KEY: MISC_FEATURE
<222> LOCATION: (15)..(15)
<223> OTHER INFORMATION: Reporter attachment site

<400> SEQUENCE: 4

Asn Glu Ala Asp Leu Glu Ala Lys Ile Arg His Leu Ala Glu Lys Leu
1               5                   10                  15

Ala Ala Arg Gly Pro Val Asp Cys Ala Gln Leu Ala Glu Gln Leu Ala
            20                  25                  30

Arg Ala Phe Glu Ala Phe Ala Arg Ala Gly
        35                  40
```

```
<210> SEQ ID NO 5
<211> LENGTH: 42
<212> TYPE: PRT
<213> ORGANISM: Artificial
<220> FEATURE:
<223> OTHER INFORMATION: 3-D15L8
<220> FEATURE:
<221> NAME/KEY: MOD_RES
<222> LOCATION: (5)..(5)
<223> OTHER INFORMATION: Nle
<220> FEATURE:
<221> NAME/KEY: MISC_FEATURE
<222> LOCATION: (8)..(8)
<223> OTHER INFORMATION: Ligand attachment site
<220> FEATURE:
<221> NAME/KEY: MISC_FEATURE
<222> LOCATION: (15)..(15)
<223> OTHER INFORMATION: Reporter attachment site
<220> FEATURE:
<221> NAME/KEY: MOD_RES
<222> LOCATION: (16)..(16)
<223> OTHER INFORMATION: Nle
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (42)..(42)
<223> OTHER INFORMATION: AMIDATION

<400> SEQUENCE: 5

Asn Ala Ala Asp Xaa Glu Ala Lys Ile Arg His Leu Ala Glu Lys Xaa
1               5                   10                  15

Ala Ala Arg Gly Pro Val Asp Cys Ala Gln Xaa Ala Glu Gln Leu Ala
            20                  25                  30

Arg Arg Phe Glu Ala Phe Ala Arg Ala Gly
        35                  40

<210> SEQ ID NO 6
<211> LENGTH: 42
<212> TYPE: PRT
<213> ORGANISM: Artificial
<220> FEATURE:
<223> OTHER INFORMATION: 4-D15L8
<220> FEATURE:
<221> NAME/KEY: MOD_RES
<222> LOCATION: (5)..(5)
<223> OTHER INFORMATION: Nle
<220> FEATURE:
<221> NAME/KEY: MISC_FEATURE
<222> LOCATION: (8)..(8)
<223> OTHER INFORMATION: Ligand attachment site
<220> FEATURE:
<221> NAME/KEY: MISC_FEATURE
<222> LOCATION: (15)..(15)
<223> OTHER INFORMATION: Reporter attachment site
<220> FEATURE:
<221> NAME/KEY: MOD_RES
<222> LOCATION: (16)..(16)
<223> OTHER INFORMATION: Nle
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (42)..(42)
<223> OTHER INFORMATION: AMIDATION

<400> SEQUENCE: 6

Asn Ala Ala Asp Xaa Glu Ala Lys Ile Arg His Leu Arg Glu Lys Xaa
1               5                   10                  15
```

```
Ala Ala Arg Gly Pro Arg Asp Cys Ala Gln Xaa Ala Glu Gln Leu Ala
         20                  25                  30

Arg Arg Phe Glu Arg Phe Ala Arg Ala Gly
         35                  40

<210> SEQ ID NO 7
<211> LENGTH: 42
<212> TYPE: PRT
<213> ORGANISM: Artificial
<220> FEATURE:
<223> OTHER INFORMATION: 1-D10L17
<220> FEATURE:
<221> NAME/KEY: MISC_FEATURE
<222> LOCATION: (10)..(10)
<223> OTHER INFORMATION: Reporter attachment site
<220> FEATURE:
<221> NAME/KEY: MISC_FEATURE
<222> LOCATION: (17)..(17)
<223> OTHER INFORMATION: Ligand attachment site

<400> SEQUENCE: 7

Asn Ala Ala Asp Leu Glu Ala Ala Ile Lys His Leu Ala Glu Ala Leu
1               5                   10                  15

Lys Glu Arg Gly Pro Glu Asp Cys Glu Gln Leu Ala Glu Gln Leu Ala
         20                  25                  30

Arg Ala Phe Glu Ala Phe Ala Arg Ala Gly
         35                  40

<210> SEQ ID NO 8
<211> LENGTH: 42
<212> TYPE: PRT
<213> ORGANISM: Artificial
<220> FEATURE:
<223> OTHER INFORMATION: 2-D10L17
<220> FEATURE:
<221> NAME/KEY: MISC_FEATURE
<222> LOCATION: (10)..(10)
<223> OTHER INFORMATION: Reporter attachment site
<220> FEATURE:
<221> NAME/KEY: MISC_FEATURE
<222> LOCATION: (17)..(17)
<223> OTHER INFORMATION: Ligand attachment site

<400> SEQUENCE: 8

Asn Ala Ala Asp Leu Glu Ala Ala Ile Lys His Leu Ala Glu Ala Leu
1               5                   10                  15

Lys Ala Arg Gly Pro Val Asp Cys Ala Gln Leu Ala Glu Gln Leu Ala
         20                  25                  30

Arg Ala Phe Glu Ala Phe Ala Arg Ala Gly
         35                  40

<210> SEQ ID NO 9
<211> LENGTH: 42
<212> TYPE: PRT
<213> ORGANISM: Artificial
<220> FEATURE:
<223> OTHER INFORMATION: 3-D10L17
<220> FEATURE:
<221> NAME/KEY: MOD_RES
<222> LOCATION: (5)..(5)
<223> OTHER INFORMATION: Nle
<220> FEATURE:
<221> NAME/KEY: MISC_FEATURE
<222> LOCATION: (10)..(10)
<223> OTHER INFORMATION: Reporter attachment site
<220> FEATURE:
<221> NAME/KEY: MOD_RES
<222> LOCATION: (16)..(16)
<223> OTHER INFORMATION: Nle
```

```
<220> FEATURE:
<221> NAME/KEY: MISC_FEATURE
<222> LOCATION: (17)..(17)
<223> OTHER INFORMATION: Ligand attachment site
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (42)..(42)
<223> OTHER INFORMATION: AMIDATION

<400> SEQUENCE: 9

Asn Ala Ala Asp Xaa Glu Ala Arg Ile Lys His Leu Ala Glu Arg Xaa
1               5                   10                  15

Lys Ala Arg Gly Pro Val Asp Cys Ala Gln Xaa Ala Glu Gln Leu Ala
            20                  25                  30

Arg Ala Phe Glu Ala Phe Ala Arg Ala Gly
            35                  40

<210> SEQ ID NO 10
<211> LENGTH: 42
<212> TYPE: PRT
<213> ORGANISM: Artificial
<220> FEATURE:
<223> OTHER INFORMATION: 4-D10L17
<220> FEATURE:
<221> NAME/KEY: MISC_FEATURE
<222> LOCATION: (5)..(5)
<223> OTHER INFORMATION: Nle
<220> FEATURE:
<221> NAME/KEY: MISC_FEATURE
<222> LOCATION: (10)..(10)
<223> OTHER INFORMATION: Reporter attachment site
<220> FEATURE:
<221> NAME/KEY: MOD_RES
<222> LOCATION: (16)..(16)
<223> OTHER INFORMATION: Nle
<220> FEATURE:
<221> NAME/KEY: MISC_FEATURE
<222> LOCATION: (17)..(17)
<223> OTHER INFORMATION: Ligand attachment site
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (42)..(42)
<223> OTHER INFORMATION: AMIDATION

<400> SEQUENCE: 10

Asn Ala Ala Asp Xaa Glu Ala Arg Ile Lys His Leu Arg Glu Arg Xaa
1               5                   10                  15

Lys Ala Arg Gly Pro Arg Asp Cys Ala Gln Xaa Ala Glu Gln Leu Ala
            20                  25                  30

Arg Ala Phe Glu Arg Phe Ala Arg Ala Gly
            35                  40

<210> SEQ ID NO 11
<211> LENGTH: 42
<212> TYPE: PRT
<213> ORGANISM: Artificial
<220> FEATURE:
<223> OTHER INFORMATION: 1-D25L22
<220> FEATURE:
<221> NAME/KEY: MISC_FEATURE
<222> LOCATION: (22)..(22)
<223> OTHER INFORMATION: Ligand attachment site
<220> FEATURE:
<221> NAME/KEY: MISC_FEATURE
```

```
<222> LOCATION: (25)..(25)
<223> OTHER INFORMATION: Reporter attachment site

<400> SEQUENCE: 11

Asn Glu Ala Asp Leu Glu Ala Ala Ile Arg His Leu Ala Glu Ala Leu
1               5                   10                  15

Glu Ala Arg Gly Pro Lys Asp Cys Lys Gln Leu Ala Glu Gln Leu Ala
            20                  25                  30

Arg Ala Phe Glu Ala Phe Glu Arg Ala Gly
        35                  40

<210> SEQ ID NO 12
<211> LENGTH: 42
<212> TYPE: PRT
<213> ORGANISM: Artificial
<220> FEATURE:
<223> OTHER INFORMATION: 2-D25L22
<220> FEATURE:
<221> NAME/KEY: MISC_FEATURE
<222> LOCATION: (22)..(22)
<223> OTHER INFORMATION: Ligand attachment site
<220> FEATURE:
<221> NAME/KEY: MISC_FEATURE
<222> LOCATION: (25)..(25)
<223> OTHER INFORMATION: Reporter attachment site

<400> SEQUENCE: 12

Asn Glu Ala Asp Leu Glu Ala Ala Ile Arg His Leu Ala Glu Ala Leu
1               5                   10                  15

Ala Ala Arg Gly Pro Lys Asp Cys Lys Gln Leu Ala Glu Gln Leu Ala
            20                  25                  30

Arg Ala Phe Glu Ala Phe Ala Arg Ala Gly
        35                  40

<210> SEQ ID NO 13
<211> LENGTH: 42
<212> TYPE: PRT
<213> ORGANISM: Artificial
<220> FEATURE:
<223> OTHER INFORMATION: 3-D25L22
<220> FEATURE:
<221> NAME/KEY: MOD_RES
<222> LOCATION: (5)..(5)
<223> OTHER INFORMATION: Nle
<220> FEATURE:
<221> NAME/KEY: MOD_RES
<222> LOCATION: (16)..(16)
<223> OTHER INFORMATION: Nle
<220> FEATURE:
<221> NAME/KEY: MISC_FEATURE
<222> LOCATION: (22)..(22)
<223> OTHER INFORMATION: Ligand attachment site
<220> FEATURE:
<221> NAME/KEY: MISC_FEATURE
<222> LOCATION: (25)..(25)
<223> OTHER INFORMATION: Reporter attachment site
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (42)..(42)
<223> OTHER INFORMATION: AMIDATION

<400> SEQUENCE: 13

Asn Ala Ala Asp Xaa Glu Ala Ala Ile Arg His Leu Ala Glu Arg Xaa
1               5                   10                  15

Ala Ala Arg Gly Pro Lys Asp Cys Lys Gln Xaa Ala Glu Gln Leu Ala
            20                  25                  30
```

```
Arg Ala Phe Glu Ala Phe Ala Arg Ala Gly
        35                  40

<210> SEQ ID NO 14
<211> LENGTH: 42
<212> TYPE: PRT
<213> ORGANISM: Artificial
<220> FEATURE:
<223> OTHER INFORMATION: 4-D25L22
<220> FEATURE:
<221> NAME/KEY: MOD_RES
<222> LOCATION: (5)..(5)
<223> OTHER INFORMATION: Nle
<220> FEATURE:
<221> NAME/KEY: MOD_RES
<222> LOCATION: (16)..(16)
<223> OTHER INFORMATION: Nle
<220> FEATURE:
<221> NAME/KEY: MISC_FEATURE
<222> LOCATION: (22)..(22)
<223> OTHER INFORMATION: Ligand attachment site
<220> FEATURE:
<221> NAME/KEY: MISC_FEATURE
<222> LOCATION: (25)..(25)
<223> OTHER INFORMATION: Reporter attachment site
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (42)..(42)
<223> OTHER INFORMATION: AMIDATION

<400> SEQUENCE: 14

Asn Ala Ala Asp Xaa Glu Ala Arg Ile Arg His Leu Arg Glu Arg Xaa
1               5                   10                  15

Ala Ala Arg Gly Pro Lys Asp Cys Lys Gln Xaa Ala Glu Gln Leu Ala
            20                  25                  30

Arg Ala Phe Glu Arg Phe Ala Arg Ala Gly
        35                  40

<210> SEQ ID NO 15
<211> LENGTH: 42
<212> TYPE: PRT
<213> ORGANISM: Artificial
<220> FEATURE:
<223> OTHER INFORMATION: 1-D37L34
<220> FEATURE:
<221> NAME/KEY: MISC_FEATURE
<222> LOCATION: (34)..(34)
<223> OTHER INFORMATION: Ligand attachment site
<220> FEATURE:
<221> NAME/KEY: MISC_FEATURE
<222> LOCATION: (37)..(37)
<223> OTHER INFORMATION: Reporter attachment site

<400> SEQUENCE: 15

Asn Glu Ala Asp Leu Glu Ala Ala Ile Arg His Leu Ala Glu Arg Leu
1               5                   10                  15

Glu Ala Arg Gly Pro Ala Asp Cys Ala Gln Leu Ala Glu Gln Leu Ala
            20                  25                  30

Ala Lys Phe Glu Lys Phe Ala Arg Ala Gly
        35                  40

<210> SEQ ID NO 16
<211> LENGTH: 42
<212> TYPE: PRT
<213> ORGANISM: Artificial
<220> FEATURE:
```

```
<223> OTHER INFORMATION: 2-D37L34
<220> FEATURE:
<221> NAME/KEY: MISC_FEATURE
<222> LOCATION: (34)..(34)
<223> OTHER INFORMATION: Ligand attachment site
<220> FEATURE:
<221> NAME/KEY: MISC_FEATURE
<222> LOCATION: (37)..(37)
<223> OTHER INFORMATION: Reporter attachment site

<400> SEQUENCE: 16

Asn Ala Ala Asp Leu Glu Ala Ala Ile Arg His Leu Ala Glu Arg Leu
1               5                   10                  15

Ala Ala Arg Gly Pro Val Asp Cys Ala Gln Leu Ala Glu Gln Leu Ala
            20                  25                  30

Ala Lys Phe Glu Lys Phe Ala Arg Ala Gly
        35                  40

<210> SEQ ID NO 17
<211> LENGTH: 42
<212> TYPE: PRT
<213> ORGANISM: Artificial
<220> FEATURE:
<223> OTHER INFORMATION: 3-D37L34
<220> FEATURE:
<221> NAME/KEY: MOD_RES
<222> LOCATION: (5)..(5)
<223> OTHER INFORMATION: Nle
<220> FEATURE:
<221> NAME/KEY: MOD_RES
<222> LOCATION: (16)..(16)
<223> OTHER INFORMATION: Nle
<220> FEATURE:
<221> NAME/KEY: MOD_RES
<222> LOCATION: (27)..(27)
<223> OTHER INFORMATION: Nle
<220> FEATURE:
<221> NAME/KEY: MISC_FEATURE
<222> LOCATION: (34)..(34)
<223> OTHER INFORMATION: Ligand attachment site
<220> FEATURE:
<221> NAME/KEY: MISC_FEATURE
<222> LOCATION: (37)..(37)
<223> OTHER INFORMATION: Reporter attachment site
<220> FEATURE:
<221> NAME/KEY: MOD_RES
<222> LOCATION: (42)..(42)
<223> OTHER INFORMATION: AMIDATION

<400> SEQUENCE: 17

Asn Ala Ala Asp Xaa Glu Ala Ala Ile Arg His Leu Ala Glu Arg Xaa
1               5                   10                  15

Ala Ala Arg Gly Pro Val Asp Cys Ala Gln Xaa Ala Glu Gln Leu Ala
            20                  25                  30

Arg Lys Phe Glu Lys Phe Ala Arg Ala Gly
        35                  40

<210> SEQ ID NO 18
<211> LENGTH: 42
<212> TYPE: PRT
<213> ORGANISM: Artificial
<220> FEATURE:
<223> OTHER INFORMATION: 4-D37L34
<220> FEATURE:
<221> NAME/KEY: MOD_RES
<222> LOCATION: (5)..(5)
<223> OTHER INFORMATION: Nle
<220> FEATURE:
<221> NAME/KEY: MOD_RES
<222> LOCATION: (16)..(16)
<223> OTHER INFORMATION: Nle
<220> FEATURE:
```

```
<221> NAME/KEY: MOD_RES
<222> LOCATION: (27)..(27)
<223> OTHER INFORMATION: Nle
<220> FEATURE:
<221> NAME/KEY: MISC_FEATURE
<222> LOCATION: (34)..(34)
<223> OTHER INFORMATION: Ligand attachment site
<220> FEATURE:
<221> NAME/KEY: MISC_FEATURE
<222> LOCATION: (37)..(37)
<223> OTHER INFORMATION: Reporter attachment site
<220> FEATURE:
<221> NAME/KEY: MOD_RES
<222> LOCATION: (42)..(42)
<223> OTHER INFORMATION: AMIDATION

<400> SEQUENCE: 18

Asn Ala Ala Asp Xaa Glu Ala Lys Ile Arg His Leu Arg Glu Arg Xaa
1               5                   10                  15

Ala Ala Arg Gly Pro Arg Asp Cys Ala Gln Xaa Ala Glu Gln Leu Ala
            20                  25                  30

Arg Lys Phe Glu Lys Phe Ala Arg Ala Gly
            35                  40
```